US008366678B2

(12) United States Patent
Bierman et al.

(10) Patent No.: US 8,366,678 B2
(45) Date of Patent: Feb. 5, 2013

(54) MEDICAL ANCHORING SYSTEM

(75) Inventors: Steven F. Bierman, Del Mar, CA (US);
Richard A. Pluth, San Diego, CA (US);
Wayne T. Mitchell, Cardiff, CA (US)

(73) Assignee: Venetec International, Inc., Covington, GA (US)

( * ) Notice: Subject to any disclaimer, the term of this patent is extended or adjusted under 35 U.S.C. 154(b) by 1303 days.

(21) Appl. No.: 11/295,903

(22) Filed: Dec. 6, 2005

(65) Prior Publication Data
US 2006/0089600 A1      Apr. 27, 2006

Related U.S. Application Data

(63) Continuation of application No. 10/452,839, filed on Jun. 2, 2003, now Pat. No. 6,972,003, which is a continuation of application No. 09/523,481, filed on Mar. 10, 2000, now Pat. No. 6,572,588.

(51) Int. Cl.
*A61M 5/32* (2006.01)
(52) U.S. Cl. ......................................... 604/180; 604/174
(58) Field of Classification Search .................. 604/174, 604/177–178, 180, 250, 263, 500, 513; 128/DIG. 6, 128/DIG. 26
See application file for complete search history.

(56) References Cited

U.S. PATENT DOCUMENTS

| | | |
|---|---|---|
| 3,167,072 A | 1/1965 | Stone et al. |
| 3,993,081 A | 11/1976 | Cussell |
| 4,082,094 A | 4/1978 | Dailey |
| 4,114,618 A | 9/1978 | Vargas |
| 4,129,128 A | 12/1978 | McFarlane |
| 4,161,177 A | 7/1979 | Fuchs |
| 4,170,995 A | 10/1979 | Levine et al. |
| 4,224,937 A | 9/1980 | Gordon |
| 4,250,880 A | 2/1981 | Gordon |
| 4,356,599 A | 11/1982 | Larson et al. |
| 4,362,156 A | 12/1982 | Feller, Jr. et al. |
| 4,397,647 A | 8/1983 | Gordon |
| 4,405,163 A | 9/1983 | Voges et al. |
| 4,453,933 A | 6/1984 | Speaker |
| 4,480,639 A | 11/1984 | Peterson et al. |
| 4,623,102 A | 11/1986 | Hough, Jr. |
| 4,659,329 A | 4/1987 | Annis |
| 4,711,636 A | 12/1987 | Bierman |
| 4,733,666 A | 3/1988 | Mercer, Jr. |
| 4,775,121 A | 10/1988 | Carty |
| 4,852,844 A | 8/1989 | Villaveces |

(Continued)

FOREIGN PATENT DOCUMENTS

| | | |
|---|---|---|
| EP | 0 931 560 | 7/1999 |
| EP | 06 12 4518 | 1/2007 |

OTHER PUBLICATIONS

Search Result, Percufix® Catheter Cuff Kit, downloaded from the Internet on Aug. 15, 2001.

*Primary Examiner* — Kevin C Sirmons
*Assistant Examiner* — Emily Schmidt
(74) *Attorney, Agent, or Firm* — Knobbe Martens Olson & Bear LLP

(57) ABSTRACT

An anchoring system for an elongated medical article comprises an anchor pad and a retainer mounted upon the anchor pad. The retainer includes a base, a cover, and a compressible member including a receptacle into which the medical article to be retained is placed. When the cover is closed, the medical article is secured within the receptacle by the pressure of the compressible member and the cover upon the medical article. One or more biasing members act upon the compressible member to increase the frictional forces acting on the retained section of the medical article. The receptacle may form a channel that follows a curved path through the retainer. The retainer may also include guide extensions to support the medical article along a transverse bend toward the skin of the patient.

23 Claims, 14 Drawing Sheets

U.S. PATENT DOCUMENTS

| | | | |
|---|---|---|---|
| 4,857,058 A | 8/1989 | Payton | |
| 4,897,082 A | 1/1990 | Erskine | |
| 4,898,587 A | 2/1990 | Mera | |
| 4,919,654 A | 4/1990 | Kalt | |
| 4,997,421 A | 3/1991 | Palsrok et al. | |
| 5,037,397 A | 8/1991 | Kalt et al. | |
| 5,084,026 A | 1/1992 | Shapiro | |
| 5,098,399 A | 3/1992 | Tollini | |
| 5,192,273 A | 3/1993 | Bierman et al. | |
| 5,192,274 A | 3/1993 | Bierman | |
| 5,226,892 A | 7/1993 | Boswell | |
| 5,266,401 A | 11/1993 | Tollini | |
| 5,308,337 A | 5/1994 | Bingisser | |
| 5,334,186 A | 8/1994 | Alexander | |
| 5,336,195 A | 8/1994 | Daneshvar | |
| 5,354,282 A | 10/1994 | Bierman | |
| 5,382,239 A * | 1/1995 | Orr et al. | 604/177 |
| 5,389,082 A | 2/1995 | Baugues et al. | |
| 5,413,562 A | 5/1995 | Swauger | |
| 5,484,420 A | 1/1996 | Russo | |
| 5,494,245 A | 2/1996 | Suzuki et al. | |
| 5,499,976 A | 3/1996 | Dalton | |
| D375,355 S | 11/1996 | Bierman | |
| 5,643,217 A | 7/1997 | Dobkin | |
| 5,681,290 A | 10/1997 | Alexander | |
| 5,685,859 A | 11/1997 | Kornerup | |
| D389,911 S | 1/1998 | Bierman | |
| 5,800,402 A | 9/1998 | Bierman | |
| 5,827,239 A | 10/1998 | Dillon et al. | |
| 5,846,255 A | 12/1998 | Casey | |
| 5,916,199 A | 6/1999 | Miles | |
| 6,015,119 A | 1/2000 | Starchevich | |
| 6,113,577 A | 9/2000 | Hakky et al. | |
| 6,206,897 B1 | 3/2001 | Jamiolkowski et al. | |
| 6,213,979 B1 | 4/2001 | Bierman | |
| 6,228,064 B1 | 5/2001 | Abita et al. | |
| 6,283,945 B1 | 9/2001 | Bierman | |
| 6,361,523 B1 | 3/2002 | Bierman | |
| 6,387,075 B1 | 5/2002 | Stivland et al. | |
| 6,387,076 B1 * | 5/2002 | Landuyt | 604/174 |

* cited by examiner

MEDICAL ANCHORING SYSTEM

RELATED APPLICATIONS

This application is a continuation of U.S. patent application Ser. No. 10/452,839 filed on Jun. 2, 2003, now U.S. Pat. No. 6,972,003, entitled "MEDICAL ANCHORING SYSTEM," which is a continuation of U.S. patent application Ser. No. 09/523,481 filed on Mar. 10, 2000, issued as U.S. Pat. No. 6,572,588 on Jun. 3, 2003, all of which are hereby expressly incorporated by reference in their entireties.

BACKGROUND OF THE INVENTION

1. Field of the Invention

This invention relates generally to a system to anchor a catheter or medical article in position upon a patient. More specifically, this invention relates to an anchoring system which retains a medical article in position upon a patient without crimping, kinking, or occluding the lumen of the medical article and which permits easy repositioning of a length of the medical article within the anchoring system.

2. Description of the Related Art

It is common in the treatment of patients to utilize catheters to introduce fluids and medications directly into the patient or to withdraw fluids from the patient. An example of a typical catheter is a percutaneous drainage tube, which is used to drain fluid from an abscess within the body. In placing a percutaneous drainage tube, it is preferable to fix the distal end of the percutaneous drainage tube as deep as possible within the abscess. As the abscess drains and closes, the percutaneous drainage tube may need to be withdrawn progressively.

During this process, the catheter may remain in place for many days. In order to secure the catheter in position at the insertion site, a healthcare worker often secures the catheter to the patient using tape. That is, the healthcare worker commonly places long pieces of tape across the portion of the catheter near the insertion site in a crisscross pattern to secure the catheter to the patient's skin. This securement inhibits unintentional migration of the distal end of the percutaneous drainage tube.

However, normal protocol requires periodic (e.g., daily) tape changes. Tape changes are also necessary if it becomes necessary to adjust the placement of the distal end of the percutaneous drainage tube as discussed above. These tape changes are time consuming, and repeated placement and removal of tape can excoriate the skin of the patient in the taped region. Because many healthcare workers find the taping procedure cumbersome and difficult to accomplish when wearing gloves, they often remove their gloves when taping. Not only does this increase the amount of time spent on the taping procedure, but it also subjects the healthcare worker to an increased risk of infection.

A variety of catheter securement devices have been developed to obviate the need for frequent application of tape to secure a catheter to a patient. One such securement device provides a flexible clamp with winged extensions that are sutured to the patient's skin. In some applications, the winged extensions are integrally formed with catheter. In other applications, the flexible clamp is covered by a rigid fitting, which receives the catheter/clamp combination in a friction-fit manner. The rigid fitting and flexible clamp are formed with lateral, aligned holes, which allow the combination to be sutured to the patient's skin. Although these suturing devices securely attach the catheter to the patient, it is obviously painful and uncomfortable for the patient. These devices are also time consuming and inconvenient to secure, pose the risk of needle-stick to the healthcare worker, and risk suture-site infection to the patient.

In addition, suture material tends to exhibit poor gripping on medical tubes and can cut through the winged extension of the flexible clamp if a rigid clamp is not used. However, the use of a rigid fitting complicates the securement procedure by adding yet another component that can be dropped on the floor and become unsterile. In addition, the sutured securement of the flexible clamp and/or the rigid fitting assembly does not permit easy release of the catheter from the patient for dressing changes and insertion site cleaning. A removal instrument (e.g., sterile scissors) also is generally required for suture removal.

One device which attempts to address these concerns is disclosed in U.S. Pat. No. 5,685,859. This device uses an adhesive pad that is attached to the skin of the patient and that surrounds the insertion site of the percutaneous drainage tube. The tube is bent over a plaster surface to lie flush with the pad and an adhesive flap is secured over the percutaneous drainage tube, holding it in place. However, it is difficult to reposition the percutaneous drainage tube when using this device. The healthcare worker must remove the adhesive flap without removing the adhesive pad, which results in poor adhesion if the same device is resealed over the tube at its new position. If a new device must be placed, then the old one must first be removed, which is even more time consuming than removing and replacing tape, and also results in excoriation of the skin.

To overcome these difficulties, the present invention involves the recognition that it would be desirable to create a securement device which releasably held a percutaneous drainage tube or other medical article in a fixed position, but which allowed for axial adjustment of the position of the medical article relative to the patient, as well as allowing the same securement device to be used over the duration of the use of a percutaneous drainage tube. The system preferably is operable without removing surgical gloves and adjustments in position can be made without the need to completely redress the insertion site.

SUMMARY OF THE INVENTION

The present anchoring system secures a medical article in a fixed position, yet permits easy repositioning of the medical article within the anchoring system, as well as easy release of the medical article from the anchoring system for dressing changes and other medical procedures. Unlike prior anchoring systems, the current anchoring system also preferably is not limited to a single medical article size. In this way the present anchoring system can be used with various medical articles having a range of sizes.

One aspect of the present invention involves an anchoring system for a medical article. The anchoring system comprises a retainer including a base and a compressible member. The base has a cavity and the compressible member is disposed within the cavity. The compressible member defines a receptacle that is configured to receive at least a portion of the medical article. At least a deformable portion of the compressible member is deformable in a manner that produces internal compressive stresses within the compressible member. These internal stresses contribute to increased normal forces that bear against the portion of the medical article that is received within the receptacle. As a result, the frictional force between the compressible member and the receive portion of the medical article is increased.

In a preferred mode, the receptacle is a channel that has a curvilinear shape. This shape furthers the frictional force acting upon the medical article when an axial force is applied to the medical article to draw it through the channel. As a result, axial movement of the medical article through the channel is further inhibited.

The anchoring system may also include at least one biasing member. The biasing member is inserted into an aperture within the compressible member and in doing so deforms at least the deformable portion of the compressible member. In this manner, the compressive force within the compressible member, which acts upon the received portion of the medical article, is produced.

The anchoring system can also be part of a catheterization system that also includes one or more medical articles. In one mode, the medical article is selected from a group consisting of catheters and tubes, and the compressible member is formed of a material that is softer than a material from which the catheter or tube is formed. For example, the compressible member can be made of a thermal plastic elastomer that has a Shore A hardness of less than 50 durometer.

The anchoring system may also include an anchor pad. The anchor pad has a first surface including an adhesive layer to adhere the pad to the patient's skin, and an opposing second surface to which the retainer is attached.

In accordance with another aspect of the present invention, an anchoring system for securing an elongated medical article to a patient is provided. The anchoring system includes an anchor pad and a retainer. The anchor pad has a first surface including an adhesive layer to adhere the anchor pad to the patient's skin, and an opposing second surface to which the retainer is attached. The retainer includes a base and a cover that is pivotally attached to the base and is movable between an open position and a closed position. A receptacle is defined between the base and the cover to receive a portion of the medical article. The receptacle has first and second longitudinal ends and is configured to engage the received portion of the medical article so as to inhibit longitudinal movement of the medical article through the receptacle. A guide extension is disposed next to one of the first and second longitudinal ends of the receptacle. The guide extension has a curvilinear surface over which the elongated medical article can track so as to smoothly transition an axial orientation of a portion of the medical article, which is adjacent to the received portion of the medical article, along the length of the adjacent portion.

In one mode, the guide extension has an arcuate shape having about a 45° arc angle. This configuration allows the guide extension to support the adjacent section of the medical article through a similar degree turn. In this manner, the medical article can extend over the patient's skin and then extend into the patient's skin in a direction that is generally skewed relative to the skin. The guide extension, however, can extend through other arc angles (e.g., 90°) so as to vary the incident angle between the medical article and the patient's skin.

The anchoring system, as noted above, can also be part of a catheterization system that also includes one or more of the medical articles. In one mode, the medical article(s) is a catheter and/or tube.

In one preferred variation of the present anchoring system, the system includes a flexible anchor pad to be attached to the skin of the patient, and a retainer which is mounted on the anchor pad. The retainer includes a base which has a cavity within which a compressible member is located. The compressible member includes a receptacle for receiving a portion of the medical article. In one preferred embodiment, the receptacle comprises a channel through the compressible member, which acts as a channel support. A cover is attached to the base by a hinge mechanism which allows the cover to be opened to allow the insertion of the medical article into the channel, or closed to prevent inadvertent motion of the medical article within the channel. The cover is held in the closed position by a latching mechanism operating between the base and the cover. At least one guide extension provides a support surface for the medical article from the end of the channel to a surface of the anchor pad to inhibit kinking of the medical article as it exits the channel of the retainer and passes through the skin of the patient.

In a further preferred variation, the anchor pad is formed into a butterfly shape which provides additional lateral and longitudinal support to the retainer and medical article by extending the anchor pad beyond the insertion site of the medical article longitudinally.

In a preferred mode of manufacture, the entire retainer is integrally formed by a two-stage, over-molding injection process, such that the base, cover, latching mechanism, and hinge mechanism are formed in the first stage from a first material, and the channel support is formed in the second stage from a second material. The first material should be elastic enough to allow the latching and hinge mechanisms to be formed from it, but rigid enough to allow the base and cover to retain their shape. The second material should be softer and compressible to allow it to deform when a medical article is pressed against it, and have a high traction surface which inhibits inadvertent longitudinal motion of the medical article within the channel. In a further mode, an inner portion of the guide extension is formed of the first material in the first stage and an outer portion of the guide extension is formed of the second material in the second stage.

In accordance with the preferred method of anchoring a medical article onto a patient, which permits an axial position of the medical article to be repositioned relative to the patient, involves inserting a section of the medical article into a channel receptacle of a compressible member of an anchoring system. A compressive force is produced within the compressible member so as to increase the normal force acting upon the inserted section of the medical article, and thereby to increase the frictional force between the inserted section of the medical article and the compressible member. A cover is positioned over at least a portion of the channel receptacle and is secured at a position overlying the portion of the channel receptacle. In this manner, the cover and the compressible member inhibit transverse movement of the medical article, and the compressible member inhibits lateral and longitudinal movement of the medical article relative to the patient.

In a preferred mode, the method also involves releasing the cover and moving the cover away from the receptacle. The medical article is then pulled through the channel receptacle so as to axially reposition at least a portion of the medical article relative to the patient. The cover is repositioned over at least a portion of the channel receptacle and is secured in this overlying position.

In accordance with another mode, a section of the medical article, which is adjacent to the inserted section of the medical article, is tracked over a curve surface to inhibit kinking of the medical article as it exits the channel receptacle and extends to the insertion site.

Further aspects, features and advantages of the present invention will become apparent from the detailed description of the preferred embodiment that follows.

BRIEF DESCRIPTION OF THE DRAWINGS

The above mentioned and other features of the invention will now be described with reference to the drawings of a preferred embodiment of the present anchoring system. The illustrated embodiment of the anchoring system is intended to illustrate, but not to limit the invention. The drawings contain the following figures.

DETAILED DESCRIPTION OF THE PREFERRED EMBODIMENT AND VARIATIONS THEREOF

The present embodiment of the anchoring system is disclosed in the context of use with an exemplary percutaneous drainage tube. The principles of the present invention, however, are not limited to percutaneous drainage tubes. It will be understood by those of skill in the art in view of the present disclosure, that the anchoring system described can be used with other types of medical articles, including, but not limited to, catheters, fluid delivery tubes, and electrical wires. For example, the anchoring system disclosed can be used to receive and secure peripheral catheters, peripherally inserted central catheters, hemodialysis catheters, surgical drainage tubes, feeding tubes, chest tubes, scopes, as well as electrical wires or cables connected to external or implanted electronic devices or sensors. One skilled in the art may also find additional applications for the devices and systems disclosed herein. Thus, the illustration and description of the anchoring system in connection with a percutaneous drainage tube is merely exemplary of one possible application of the anchoring system.

Figure 1:
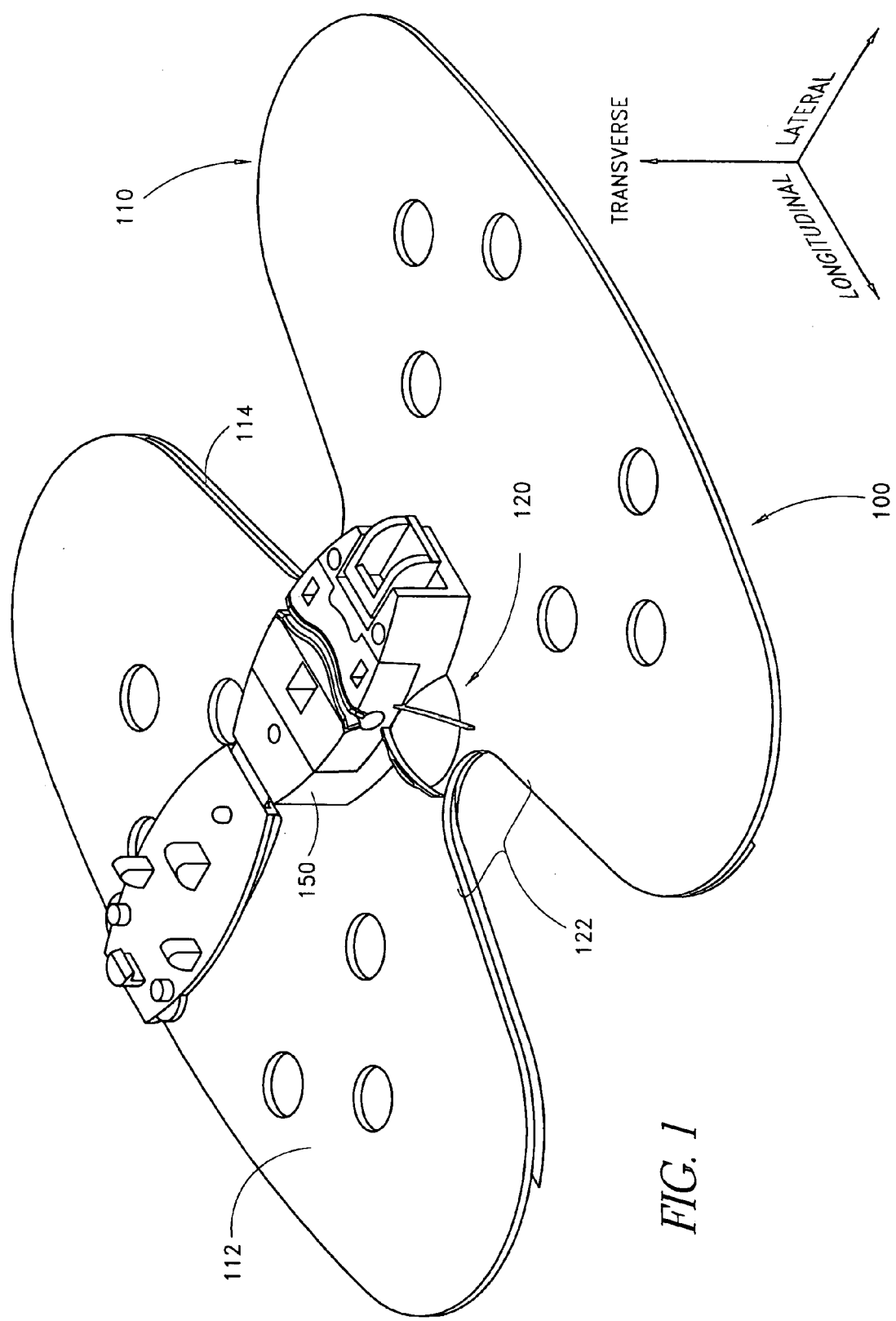
FIG. 1 shows a perspective view of an anchoring system that is configured in accordance with a preferred embodiment of the present invention, and which illustrates a retainer mounted on an anchor pad of the anchoring system with a cover of the retainer in an open position.

To assist in the description of these components of the anchoring system (see FIG. 1), the following coordinate terms are used. A "longitudinal axis" is generally parallel to the section of the tube retained by the anchoring system 100. A "lateral axis" is normal to the longitudinal axis and is generally parallel to the plane of an anchor pad 110, as seen in FIG. 1. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the medical article, and therefore is substantially synonymous with the term "longitudinal" as used herein. Also, the terms "proximal" and "distal", which are used to describe the present anchoring system, are used consistently with the description of the exemplary applications. Thus, proximal and distal are used in reference to the center of the patient's body. The terms "upper," "lower," "top," "bottom," and the like, which also are used to describe the present anchoring system, are used in reference to the illustration orientation of the embodiment. A detailed description of a preferred embodiment of the anchoring system, and its associated method of use, now follows.

Overview of the Anchoring System

As shown in FIG. 1, the described embodiment comprises an anchoring system 100 in two main components: the anchor pad 110 and a retainer 120. As noted above, the anchoring system can form a component of a catheterization system that also includes one or more medical articles (e.g., a percutaneous drainage tube).

The retainer is mounted upon the anchor pad 110 and the anchor pad is secured to the skin of the patient, generally by an adhesive disposed upon the bottom surface of the pad. The retainer 120 receives the medical article and secures it in position. The retainer itself comprises several sub-components (see FIG. 7), including a base 150, a cover 200, a compressible member 250, and one or more guide extensions 300. The releasable engagement of the medical article is achieved, at least in part, by cooperation between the compressible member 250, the base 150 and the cover 200. Because the cover may be opened after the tube is secured, it is possible for the tube to be removed from the anchoring system 100 for any necessary purpose, such as to reposition the distal end of the drainage tube (as described below), to change the dressing at the insertion site, or to facilitate moving the patient. This removal of the tube from the anchoring system 100 can be accomplished without removing the anchoring system from the patient.

The tube is held in position through a combination of lateral and transverse pressure along the length of the tube within a receptacle of the compressible member 250. In the illustrated embodiment, the receptacle comprises a channel 260, the lateral pressure being provided by the sides of the channel, and the transverse pressure being provided by the bottom and upper portions of the channel and the cover 200 (see FIG. 18). When the cover 200 is closed and secured into the closed position by the latching mechanism 350 (see FIG. 10), these forces inhibit the tube from moving substantially in either the lateral or transverse directions. Longitudinal motion of the tube is inhibited by the friction of the channel 260 against the outside walls of the tube. Because these forces are provided along a length of the retained tube, rather than being concentrated on a few small points, the lumen of the percutaneous drainage tube is not occluded. To further increase the resistance to axial motion of the tube, the channel 260 is curved along its length to increase the frictional force which will be imposed upon the percutaneous drainage tube, as will be discussed in greater detail below. Additional resistance can be obtained by increasing the compression on the compressible member—either by greater interference between the retained section of the medical article or by applying a compressive force to the compressible member (e.g., by biasing member)—or by adhesives or surface treatment covering at least a portion of a channel or cover wall that contacts the medical article, as explained below.

Furthermore, the embodiment described provides a universal feature such that the anchoring system 100 can be used to receive and secure a variety of sizes of medical articles. Because the securing forces are provided along the length of the tube which is placed within the channel 260 of the retainer 120, any tube which can be placed within the channel 260 can be suitably retained by the anchoring system 100. The pliant nature of the compressible member 250 also allows for the channel 260 to stretch to accommodate tubes of diameter slightly larger than that of the channel itself.

Anchor Pad

Figure 2A:
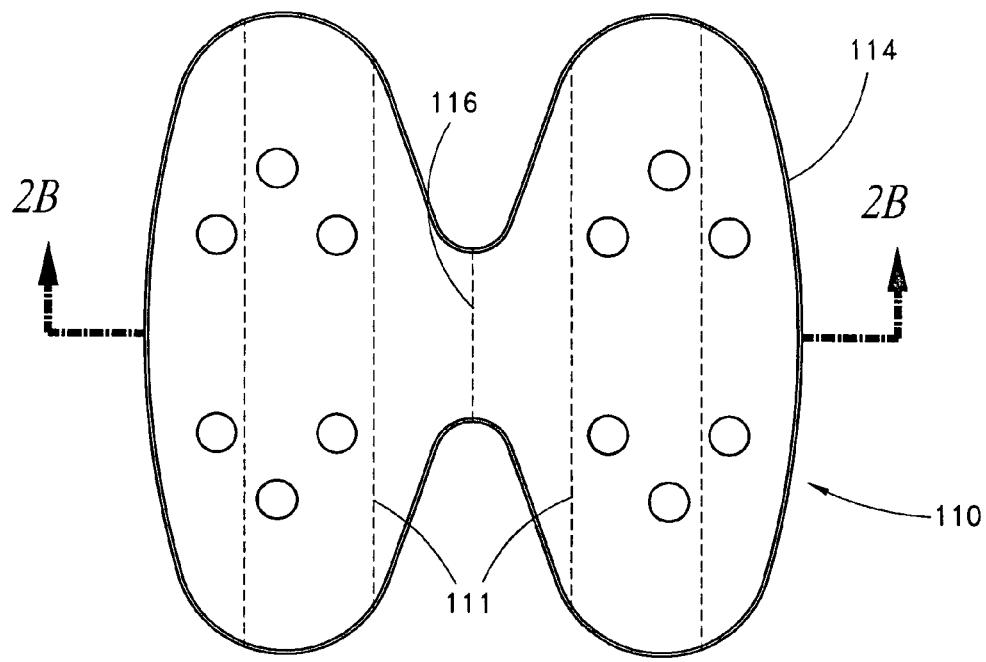
FIG. 2A shows a top plan view of the anchor pad of FIG. 1.
Figure 2B:
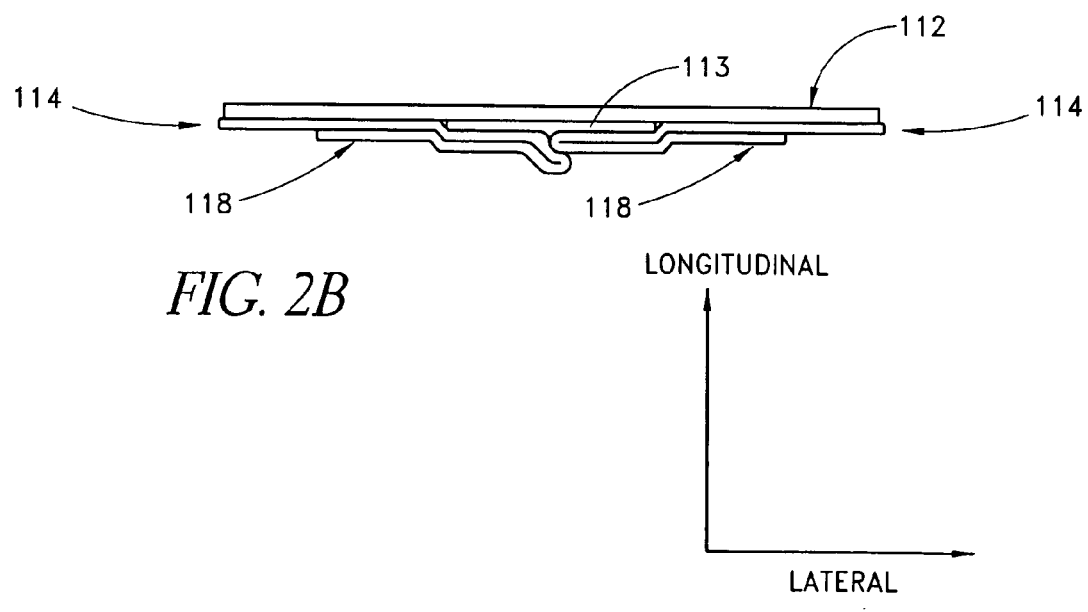
FIG. 2B shows a cross-sectional view of the anchor pad and release liner of FIG. 2A, taken along line 2B-2B.

As is seen in FIGS. 2A and 2B, the anchor pad 110 is a substantially flat piece of material with transversely opposing sides. The proximal, or lower, side of the pad faces toward the skin of the patient, and is preferably covered with an adhesive surface suitable for attaching the anchor pad 110 to the skin of the patient. The upper or distal side 112 of the anchor pad 110 faces away from the skin of the patient and supports the retainer 120.

The anchor pad 110 preferably comprises a laminate structure with an upper foam layer (e.g., closed-cell polyethylene foam) and a lower adhesive layer. The lower adhesive layer constitutes the lower surface of the anchor pad 110. The lower surface desirably is a medical-grade adhesive and can be either diaphoretic or nondiaphoretic, depending upon the particular application. Such foam with an adhesive layer is available commercially from Tyco Adhesives of Norwood, Mass.

A surface of the upper foam layer constitutes the upper surface 112 of the anchor pad 110. The upper surface 112 can be roughened by chemical priming or corona-treating the foam with a low electric charge. The roughened or porous upper surface 112 can improve the quality of the adhesive joint (which is described below) between the base 120 and the anchor pad 110. In the alternative (not shown), the flexible anchor pad 110 can comprise a medical-grade adhesive lower layer, an inner foam layer and an upper paper or other woven or nonwoven cloth layer.

As shown in FIGS. 2A and 2B, the lower surface of the anchor pad 110 also includes a region of hydro-colloid 113 adhesive disposed centrally on the anchor pad 110 and extending in the longitudinal direction. This hydro-colloid 113 region provides an adhesive which is less irritating to sensitive skin on the portion of the anchor pad 110 which is closest to the insertion site.

A removable paper or plastic release liner 114 desirably covers the adhesive lower surface before use. The release liner 114 preferably resists tearing and desirably is divided into a plurality of pieces to ease attachment of the anchor pad 110 to a patient's skin. In the illustrated embodiment, the release liner 114 is split along a centerline 116 of the anchor pad 110 in order to expose only half of the adhesive lower surface at one time.

The length of each release liner piece, as measured in the lateral direction, extends beyond the centerline 116 of the anchor pad 110 and is folded over, or back onto the release liner 114. This folded over portion defines a pull-tab 118 to facilitate removal of the release liner 114 from the adhesive lower surface. A healthcare worker uses the pull-tab 118 by grasping and pulling on it so that the release liner 114 is separated from the lower surface. The pull-tab 118 eliminates the need to pick at a corner edge or other segment of the release liner 114 in order to separate the release liner from the adhesive layer. The pull-tab 118 of course can be designed in a variety of configurations. For example, the pull-tab need not be located along a centerline 116 of the anchor pad 110; rather, the pull-tab 118 can be located along any line of the anchor pad 110 in order to ease the application of the anchor pad onto the patient's skin at a specific site. For example, an area of a patient's skin with an abrupt bend, such as at a joint, can require that the pull-tab 118 be aligned toward one of the lateral ends of the anchor pad 110 rather than along the centerline 116.

The anchor pad 110 also preferably includes a concave section 122, as shown in FIG. 1, that narrows the center of the anchor pad 110 proximate to the retainer 120. In the illustrated embodiment, the anchor pad 110 is formed generally into a butterfly shape that includes a concave section 122 on each side of the retainer 120. This shape permits the anchor pad 110 to be placed on the patient such that the arms of the butterfly extend beyond the insertion site one side, and away from the insertion site on the other. By aligning the anchor pad and the insertion site of the medical article in this way, the greatest possible stability is provided to the tube. This also minimizes the free length of tube between the insertion site and the channel 260 of the retainer (described below), helping avoid the tube being inadvertently caught or pulled and dislodged as the patient moves or as healthcare workers tend the patient.

The retainer 120 is preferably centered upon the anchor pad 10 about an axis which bifurcates the butterfly shape. Consequently the lateral sides of the anchor pad have more contact area with the skin, both forward and rearward of the retainer 120 in the longitudinal direction, which provides greater stability and adhesion to a patient's skin while still permitting the retainer 120 to be located near the insertion site. The anchor pad 110 also can include suture and/or breather holes to the sides of the retainer 120, as shown in FIGS. 1 and 2A.

Retainer Base

Figure 4:
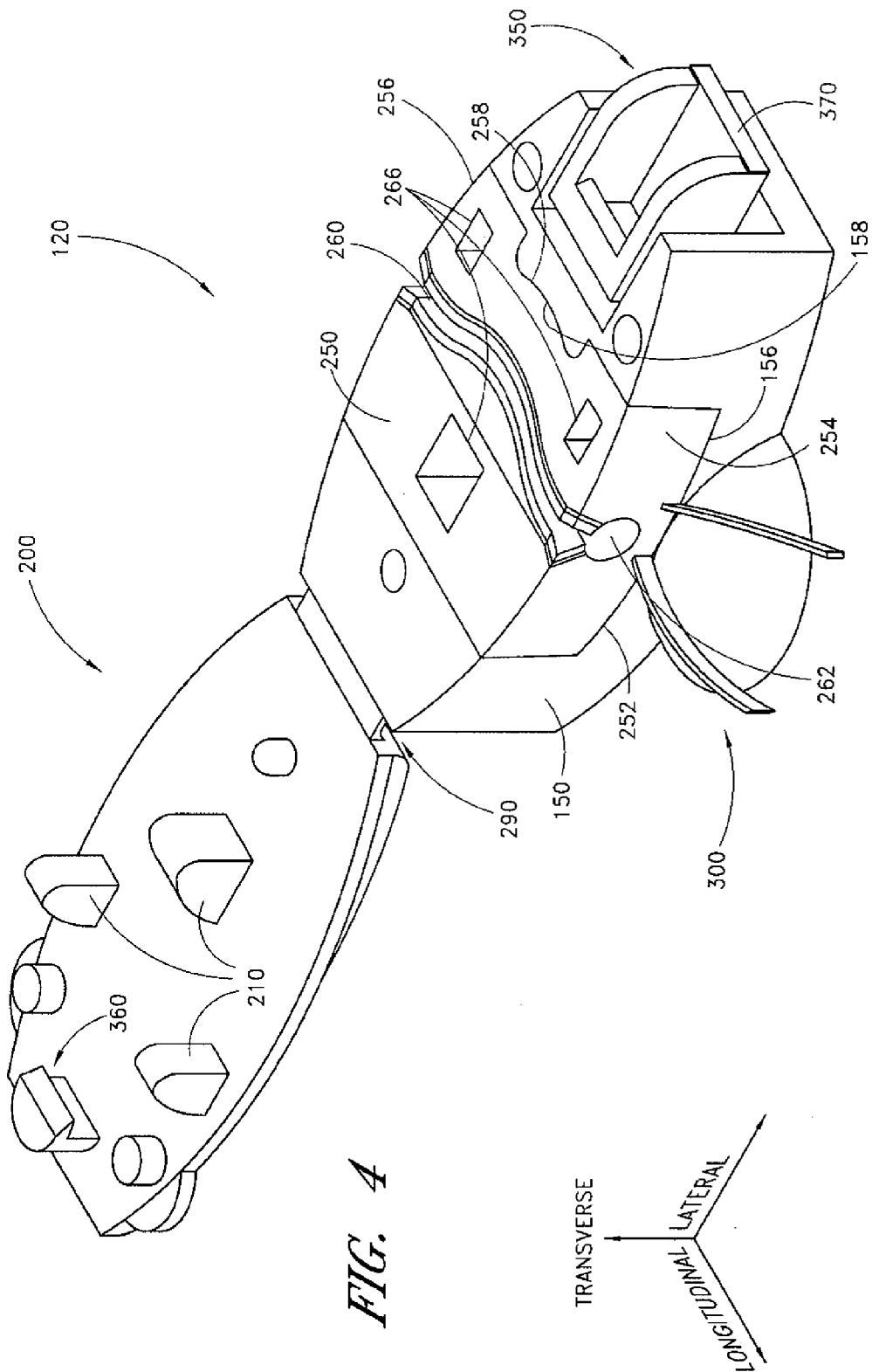
FIG. 4 shows an enlarged perspective view of the retainer of FIG. 1 with the cover in the open position.

FIG. 4 shows a more detailed view of the retainer 120 of a preferred embodiment of the present invention. The retainer 120 includes substantially rigid structure formed by the base 150 and cover 200, as well as components with some flexibility, such as the hinge 290 and latching mechanism 350. Additionally, the retainer 120 includes components which are more elastic and pliant, specifically, a compressible member 250. In a preferred mode, a surface 320 of the guide extension(s) 300 is also more elastic and pliant than an inner portion of the guide extension 300. In the illustrated embodiment, the base 150, cover 200, hinge 290, guide member inner portion and latching mechanism 350 are formed integrally to comprise a single piece. This can be accomplished in any of a variety of ways well known to those skilled in the art. For instance, the base 150, cover 200, hinge 290, and latching mechanism 350 can be injection molded in order to reduce fabrication costs. The entire retainer 120 may also be formed using a two-stage over-molding process utilizing different materials in each stage of the molding. In this way, the entire retainer 120 may be formed integrally, allowing the compressible member 250 and outer surface 320 of the guide extensions 300 to be formed of a different material than the less pliant material used for the remainder of the retainer 120. Appropriate materials and manufacturing techniques are described below.

As shown in FIG. 4, a base 150 in the illustrated embodiment comprises an elongated solid body of a generally parallelepiped shape. The base can, however, be configured in a wide variety of shapes, such as circular, square, or triangular in order to suit a particular application. The longitudinal dimension of the base 150 is desirably sufficiently long to provide stability to the percutaneous drainage tube along its retained length. That is, the longitudinal length of the retained tube is sufficient to inhibit rocking of the tube relative to the retainer 120 (i.e., to prevent the retainer from acting as a fulcrum for the percutaneous drainage tube). Also, the lateral dimension of the base 150 desirably allows the healthcare worker to easily and naturally grip the base. The base 150 is also desirably sized so as to accommodate locating the hinge 290 and a portion of the latch mechanism 350 upon it.

Figure 5:
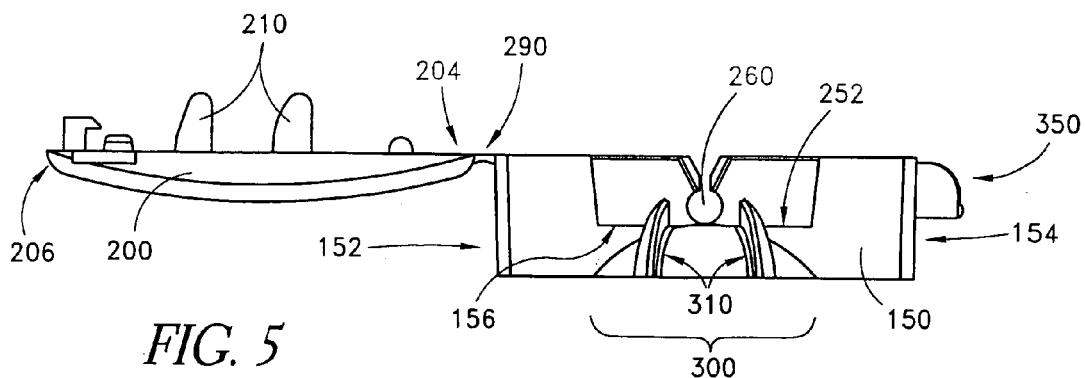
FIG. 5 shows a front elevational view of the retainer of FIG. 1 with the cover in the open position.

With reference to FIG. 5, the base 150 includes a first end 152 and a second end 154. The first end 152 lies generally at one lateral end of the base 150, and the second end 154 lies at an opposite lateral end of the base 150. A cavity 156 is formed on the base 150 between the first end 152 and the second end 154. This cavity 156 receives the compressible member. In the present embodiment, the compressible member takes the form of a channel support 250, in which a receptacle 260 for receiving a portion of the medical article is located. The compressible member and receptacle will be discussed in greater detail below. In the illustrated embodiment, the cavity 156 has a generally rectangular longitudinal cross section, with a projection 158 which interacts with corresponding geometry upon the channel support 250 to secure and stabilize the channel support 250 upon the base 150 as described below. The cavity 156 forms a substantially rectangular path from one longitudinal wall of the base 150 to the other. The upper surface of the base 150 is higher than the bottom of the cavity 156, and these higher areas are located lateral of the cavity 156 form the first end 152 and second end 154 of the base 150 of the retainer 120.

The side walls which are located lateral of the cavity 156 are angled slightly from the vertical. In the embodiment illustrated in FIG. 5, these walls angle laterally outward from bottom to top. This arrangement facilitates the removal of the base 150 from the molding machine used to manufacture it. The illustrated embodiment makes use of an approximately 5° angle from the vertical, but those skilled in the art will recognize that angles both larger and smaller than 5° may serve a similar purpose.

The base 150 is attached to the upper surface 112 of the anchor pad 110. The bottom surface 160 of the base is desirably secured to the upper surface 112 of the anchor pad 110 by a solvent bond adhesive, such as cyanoacrylate or other bonding material. One such adhesive is available commercially as Part No. 4693 from the Minnesota Mining and Manufacturing Company (3M).

Retainer Compressible Member

The compressible member includes a receptacle to receive at least a portion of the medical article to be retained. As can be seen in FIGS. 4 and 5, the compressible member of the illustrated embodiment takes the form of a channel support 250 which comprises a substantially parallelepiped shape. The channel support 250 is located within the cavity 156 of the base 150 of the retainer 120 described above. Although the illustrated preferred embodiment discloses a channel support 250 used as a compressible member, other forms of compressible member may also be used when practicing the present invention.

In the illustrated embodiment, the channel support 250 is of a substantially rectangular cross section in order to appropriately interact with the illustrated base 150. It will, however, be understood by those skilled in the art that the cross section of the cavity 156 need not be substantially rectangular, so long as the cavity cross section matches that of the lower surface 252 of the channel support 250 (or other compressible member) so as to properly secure and stabilize the channel support 250 upon the base 150.

Furthermore, the channel support 250 (or other compressible member) need not lie within a cavity on the base 150 of the retainer 120. The compressible member can be effectively disposed upon the cover 200 of the retainer in another mode of the present invention. It is also possible that the compressible member can be divided into two or more pieces some of which are disposed upon the cover and some of which are disposed upon the base. Those skilled in the art will recognize that these and other varied placements of the compressible member can be used when practicing the current invention.

The channel support 250 preferably extends from the bottom of the cavity 156 in the transverse direction to a height such that the channel support 250 is flush with the top of the base 150. The channel support 250 has a first end 254 and a second end 256, which are located longitudinal of the center of the channel support 250. These first and second ends 254, 256 of the channel support 250 preferably lie substantially flush with the edges of the base 150 in the embodiment shown. Those skilled in the art will recognize that the channel support 250 need not lie completely flush with the base 150 in all modes.

For example, the channel support 250 may extend beyond the longitudinal extent of the base 150, or may not extend to the edge of the cavity 156 in a longitudinal direction. Similarly, in some embodiments it may be advantageous for the channel support 250 to be slightly thicker in the transverse direction than the cavity 156 is transversely deep. This will provide an additional spring force upon the cover 200 of the retainer 120 to provide a bias toward the open position, as well as provide compression upon the channel 260 when the cover 200 is moved into the closed position.

The channel support 250 also comprises geometry that interacts with the projection 158 of the base 150 in order to support and stabilize the channel support 250 upon the base 150. In the illustrated embodiment, this geometry comprises a slot 258 which interacts with the projection 158 of the base 150. Those skilled in the art will recognize that other interacting geometry will serve equally well as long as the geometry of the channel support 250 is made to correspond to the geometry of the base 150.

With reference to FIG. 4, the channel support 250 additionally comprises a receptacle for receiving a portion of the medical article to be retained. In the illustrated embodiment, this receptacle takes the form of a longitudinal channel 260 that extends from the first end 254 of the channel support 250 to the second end 256 of the channel support 250. The channel 260 has a truncated circular cross-section and is exposed along its upper surface, i.e., the channel is transversely accessible along its length from above. The truncated shape gives the channel 260 an upper opening. Although the receptacle takes the form of a channel in the described preferred embodiment of the present invention, those skilled in the art will recognize that receptacles of other forms are also possible.

This upper opening into the channel 260 is chamfered to make insertion of a medical device into the channel from above easier. In addition, the chamfer 268 on the convex side of the channel 260 extends farther laterally near the longitudinal midpoint of the channel than the chamfer on the concave side of the channel. With this enlarged convex side chamfer 268, a medical article, which is pressed directly downward, is more smoothly directed into the channel 260, even in the region where the channel is laterally displaced from the axis between the ends 262, 264 of the channel 260.

Figure 7:
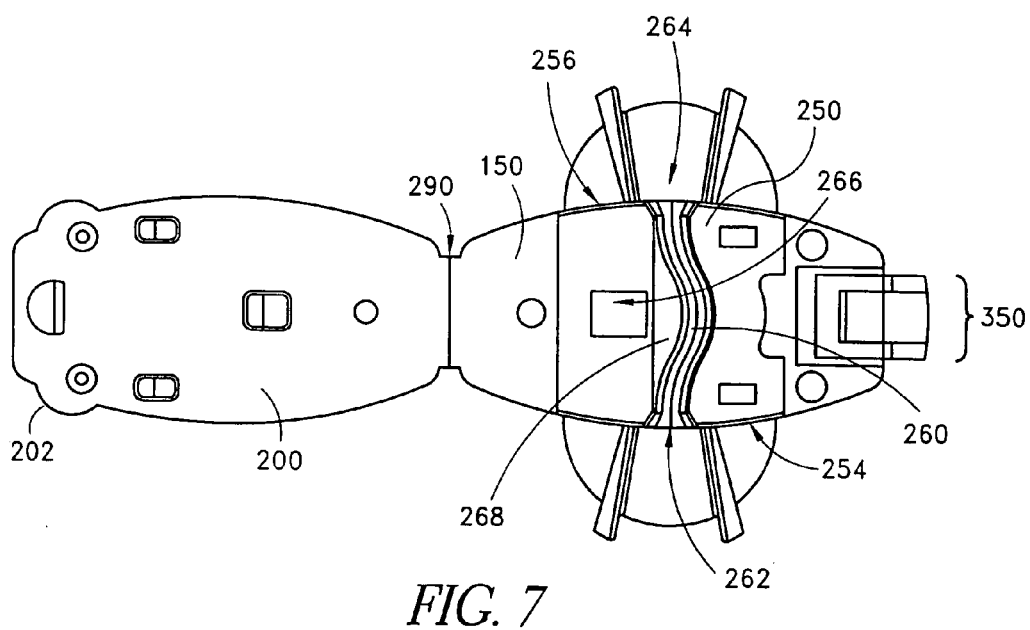
FIG. 7 shows a top plan view of the retainer of FIG. 1 with the cover in the open position.

As seen in FIG. 7, the channel 260 follows a laterally curved path from one end 254 of the channel support 250 to the other end 256. Even though the ends 262, 264 of the channel 260 are axially perpendicular to their respective ends 254, 256 of the channel support 250, the channel 260 is laterally displaced to one side and then back to the center as it passes through the channel support 250.

Figure 8:
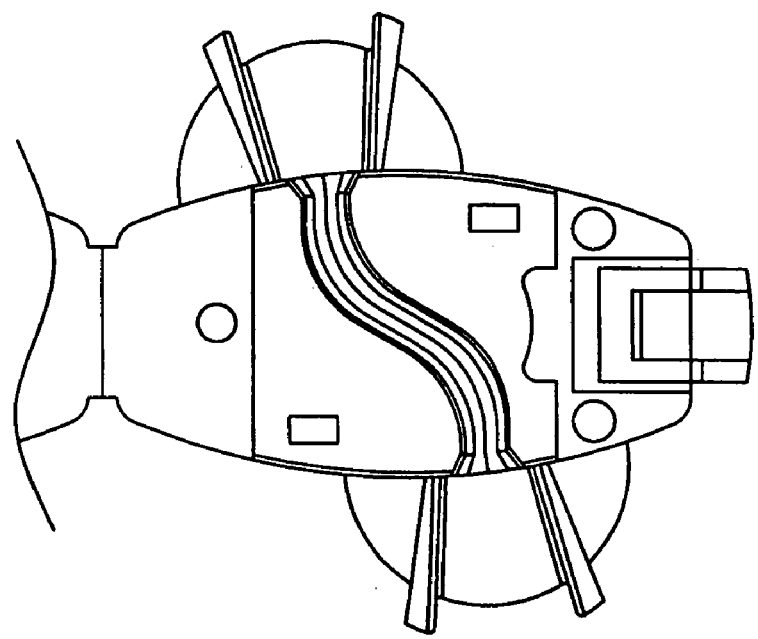
FIG. 8 shows a top plan view of the base and a compressible member of an additional variation with a single S-shaped channel.
Figure 9:
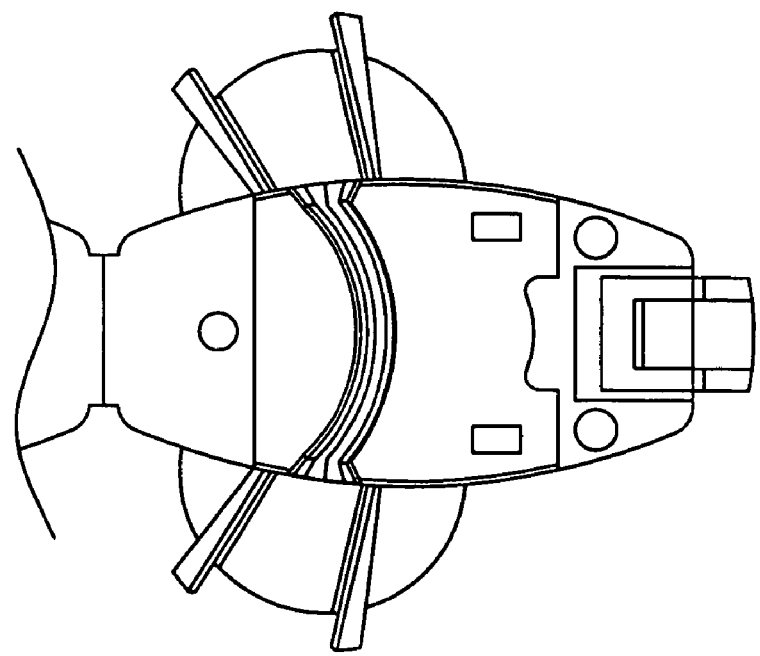
FIG. 9 shows a top plan view of the base and a compressible member of another variation embodiment with a single C-shaped channel.

This serpentine curve in the channel 260 increases the friction which is applied to walls of the retained tube, as will be discussed below. Although the illustrated channel curves to one side and then back in a serpentine shape, those skilled in the art will understand that other curved paths will serve a similar purpose. For example, an S-shaped curve as shown in FIG. 8 can also be used in practicing the present invention. In the S-shaped curve, the ends of the channel are not aligned laterally with one another, and the channel curves first in one direction and then the other in passing through the compressible member. Another example of a possible channel design is a C-shaped curve, as shown in FIG. 9. In the C-shaped curve, the path of the channel is not perpendicular to the ends of the channel, and the channel curves in only one direction as it passes through the compressible member. Various other shapes for channels will be apparent from the above to those skilled in the art. In addition, the retainer can includes separate channel sections that are staggered relative to one another in a form similar to that shown and described in U.S. Pat. No. 5,800,402, issued Sep. 1, 1998, which is hereby expressly incorporated by reference.

Figure 20:
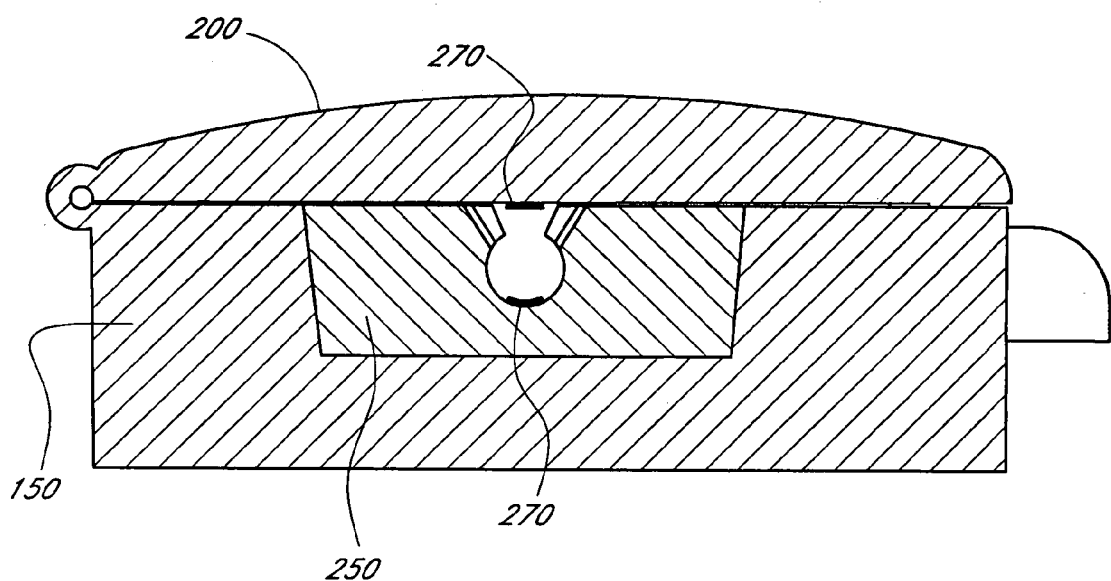
FIG. 20 illustrates a cross-sectional view of the retainer of FIG. 18 with the percutaneous drainage tube removed and shows adhesive layers located on the cover and on the base.

Additionally, the channel 260 may include an adhesive or a surface treatment, such as, for example, the adhesive layer 270 shown in FIG. 20, which is applied to the inner surface of the channel to further increase the friction between the channel support 250 and the secured section of the medical article. Suitable surface treatments include those which increase the "grip" provided by the channel walls, for example by creating a high friction surface within the channel. Examples of such treatments include, without limitation, corona treating, chemical treating, scoring, and adhesive treating. The surface treatment can also be molded into the channel surface (e.g., ridges).

Appropriate adhesive treatments are those which provide for releasable traction, rather than permanent bonding, between the channel support and the medical article. Such adhesive treatments include hot-melt adhesives which retain a soft tacky surface at room temperature. Those skilled in the art will recognize that adhesives other than hot-melt adhesives may serve a similar function. The adhesive may be disposed upon the channel 260 (or other receptacle of the compressible member) by various means, including being applied to the surface from above after the channel 260 is formed, spraying the adhesive into the channel, and injecting the adhesive into the channel from below through a hole that extends through the bottom of the compressible member 250 and base 150 of the retainer 120. The latter method is best suited to hot melt adhesives, although various other methods known in the art may be adapted for use with any of the above application methods.

The channel support 250 also comprises apertures 266 which accept the biasing members 210 of the cover (described below). The apertures 266 are disposed within the channel support 250 (or other compressible member) laterally spaced apart from the channel 260. Generally, an aperture is preferably located toward the center of curvature of a curved portion of the channel 260. This helps more evenly distribute the compressive stresses created in the channel support 250 by the biasing members 210 as will be explained below.

In the preferred embodiment, as seen in FIGS. 4 and 7, the apertures 266 are disposed on alternate lateral sides of the channel 260 as the channel passes through the channel support 250 from its first end 262 to its second end 264. As the channel 260 moves away from its first end 262, it can be seen to curve to the right. An aperture 266 is disposed to the right of the channel 260 in this region of the channel support 250. In the longitudinal center of the channel support 250, the path of the channel 260 curves to the left. Another aperture 266 is disposed to the left of the channel 260 in the longitudinally central region of the channel support 250. As the channel 260 approaches its second end 264, it once again curves to the right. The third aperture 266 is disposed to the right of the channel 260 in this region of the channel support 250.

By spacing the apertures 266 on alternate sides of the channel 260 and curving the path of the channel around the positions of the apertures in this way, the channel remains at a more constant distance from the apertures 266. When the channel support 250 is subject to compressive stresses (as will be discussed below), this will result in more even compression along the length of the channel 260.

Another example showing the manner in which the channel is made to weave between the apertures in the channel support can be seen in FIG. 8, which discloses an S-shaped channel. As the channel progresses through the channel support it curves first to the left and then to the right. To accommodate this, the first aperture is located to the left of the channel, and the second aperture is located to the right of the channel. Those skilled in the art will appreciate that this effect can be achieved on a channel of arbitrary shape by placing the apertures toward the side to which the channel curves at any point along its length.

Retainer Guide Extension

The retainer includes one or more guide extensions 300 that are disposed adjacent to the base 150. They comprise solid extensions which extend from the longitudinal sides of the base 150 to the upper surface 112 of the anchor pad 110. As can be seen in FIGS. 4 and 5, each guide extension 300 is shaped substantially as a partial surface of an elongate spheroid. The illustrated embodiment shows the use of two guide extensions 300, one on each side of the base 150. It is also possible to produce embodiments of the present invention which make use of only a single guide extension or more than two guide extends. In addition, the guide extends need not be disposed on opposite sides of the retainer from each other; for instance, where the channel extends through a 90 degree turn, one of the guide members can be disposed on a lateral side while the other guide member can be disposed on an adjacent longitudinal side of the retainer.

As shown in FIG. 5, the guide extensions 300 extend transversely from the level of the bottom surface 160 of the base 150 to the bottom of the channel ends 262, 264 on the side of the channel support 250. Seen in profile, as in FIG. 6, the guide extensions 300 gradually curve downward from the height of the channel 260 to the level of the bottom surface 160 of the base 150 as the guide extension 300 extends away from the side of the base 150. This places the lowest portion of the surface of the guide extension 300 even with the upper surface 112 of the anchor pad 110. As the guide extension 300 extends away from the side of the base, a support surface 320 (shown in FIG. 10) angles more toward the vertical direction. Preferably the angle θ between the lowest portion of the surface 320 of the guide extension 300 and the anchor pad 110 will approximate the incident angle at which the medical article exits the skin of the patient. This angle θ will preferably be between about 5° and about 90°, and more preferably between about 30° and about 45°.

Each guide extension 300 further comprises a pair of guide ridges 310 which protrude from the surface 320 of the guide extension 300. These guide ridges 310 are spaced apart from one another by at least the width of the channel 260 and run generally longitudinally along the guide extension 300. The guide ridges 310 generally flare outward from the centerline of the guide extension 300 as they move down toward the upper surface 112 of the anchor pad 110, as shown in FIG. 7.

Figure 10:
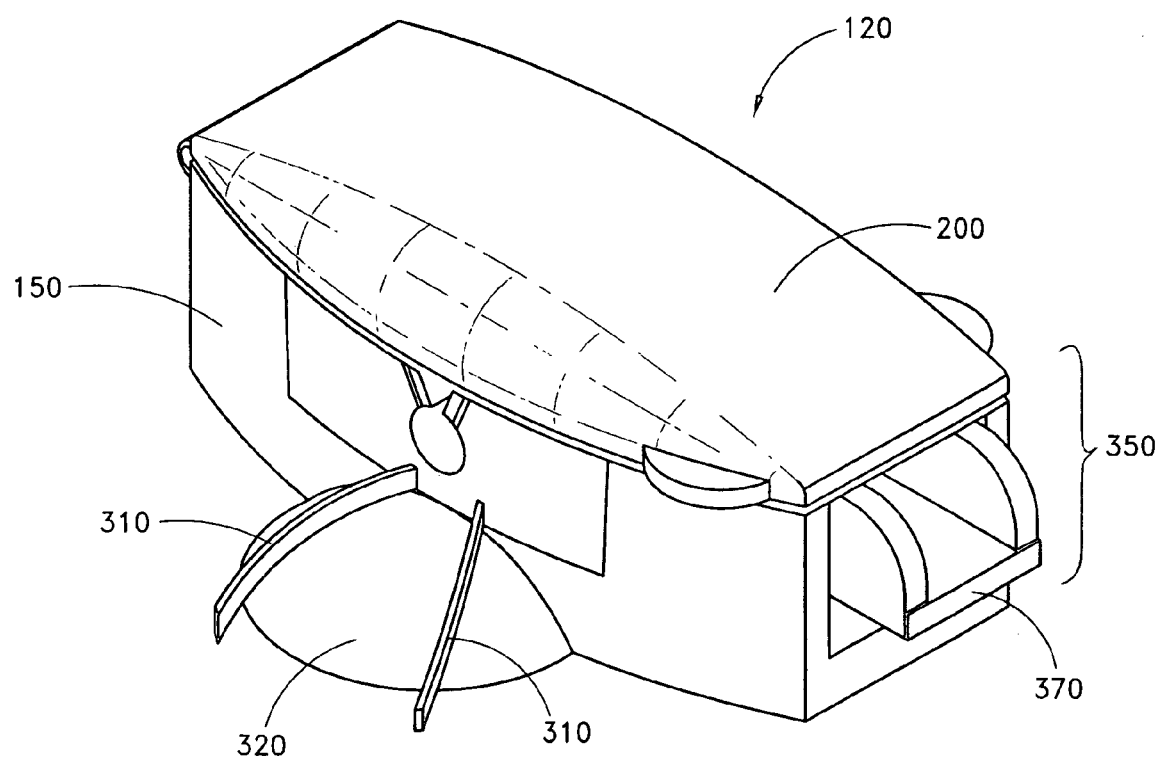
FIG. 10 shows a perspective view of the retainer of FIG. 4 with the cover in the closed position.

This flared geometry accommodates small misalignments in the placement of the anchor pad 110 upon the skin of the patient. By flaring the guide ridges 310 apart as they approach the upper surface 112 of the anchor pad 110, the insertion site need not be directly in line with the centerline of the ends 262, 264 of the channel 260. The upper surface of the guide extension 300 between the guide ridges 310 forms the support surface 320 upon which the medical article will lie, as seen in FIG. 10.

The flared geometry of the guide ridges 310 also accommodates the natural shifting which can take place as the skin of the patient moves over the musculature or other internal structure in the region near the insertion site. Because percutaneous drainage tubes and other medical articles often penetrate well beyond the skin, the distal end of the percutaneous drainage tube will tend to remain fixed relative to the internal structure into which it is inserted. However, as the skin shifts, the exact positioning and angle of penetration of the medical article may also shift. This may introduce relative displacements between the anchoring system 100 and the insertion site. By flaring the guide ridges 310, small shifts do not pull the medical article off of the support surface 320 of the guide extensions. This can be particularly pronounced if the insertion site is in a swollen area or near a joint such as an elbow.

In this way, the guide extensions 300 provide a gradually descending support surface 320 upon which the tube to be retained will lie as it extends from running substantially parallel to the skin of the patient inside the channel 260 of the retainer 120, to running at an angle which may be at an incident angle of up to 90°. The guide extension helps secure the medical article as will be described below.

It is preferable that the guide extensions 300 generally, and the outer support surface 320 in particular, are formed from a soft, pliant material similar in properties to that used in the compressible member 250. This material will help distribute any force of the support surface 320 against the medical article evenly, so as to avoid producing abrupt stress concentrations which could lead to crimping or buckling, or occlusion of the lumen of the medical article. This material will also add further frictional forces which help inhibit longitudinal motion of the medical article within the retainer. The inner bases of the guide extensions 300, however, are formed of a more rigid material to support the outer support surface 320 and the overlying section of the medical article.

Retainer Cover

As seen in FIG. 7, the cover 200 has an elongate shape which desirably is coextensive with the planar size and shape of the base 150 (i.e., desirably has the same geometric shape and size as the base); however, the cover 200 need not be the same size or shape as the base 150. For instance, the cover 200 can be sized to extend beyond any lateral, transverse, or longitudinal edge of the base 150 or, alternatively, can be sized so as to not extend to the lateral, transverse, or longitudinal edge of the base. The cover 200 can also include a skirt (not shown) or a flange 202 that extends over and/or about the base 150 or any portion thereof. As shown in FIG. 7, this flange 202 makes it easier for a healthcare worker to grip and manipulate the cover 200.

The cover 200 desirably has a sufficient size to cover the channel support 250 in the base 150 and to accommodate a portion of the latch mechanism 350 and the hinge 290 which operates between the base 150 and the cover 200, as described below. While the cover 200 need not cover the entire channel support 250, it is preferable that the cover 200 lie above at least a portion of the channel 260 so as to help retain the medical article and to inhibit transverse motion of the medical article out of the channel 260. The cover 200 also desirably is of a dimension which provides for easy manipulation. For example, the cover's size easily accommodates the grasp of a healthcare worker.

The cover 200 is connected to the base 150 by at least one hinge 290 to provide the cover with at least two positions: an open position as shown in FIG. 4, in which the channel 260 is exposed transversely from above allowing a medical article to be inserted therein; and a closed position shown in FIG. 10, in which the cover 200 is located over the base 150 and at least part of the channel support 250, and preferably covers at least a portion of the channel 260. In the closed position, the cover 200 is held in place by a latch mechanism 350, described below, to inhibit the unintentional transverse release of a medical article from the channel 260.

With reference to FIG. 5, the cover 200 includes a first end 204 which lies generally at one lateral end of the cover 200. The first end 204 of the cover 200 therefore generally corresponds to the first end 152 of the base 150. The cover 200 also has a second end 206. The second end 206 lies generally toward the other lateral end of the cover 200 opposite of the first end 204, and corresponds generally to the second end 154 of the base 150.

Figure 6:
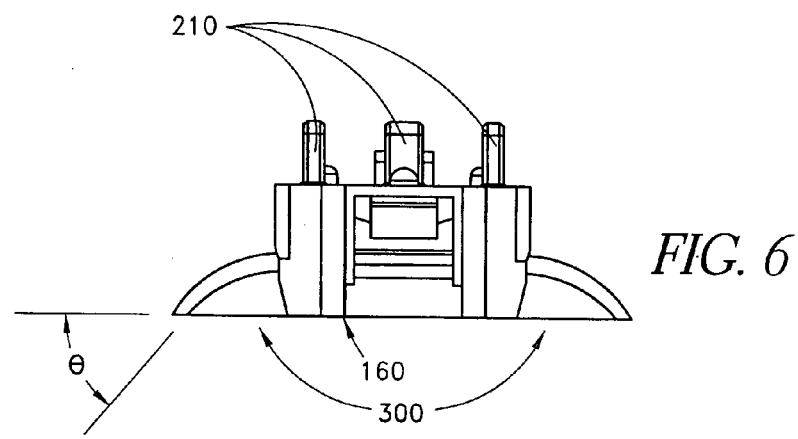
FIG. 6 shows a side elevational view of the retainer of FIG. 1 with the cover in the open position.

The cover 200 also comprises a plurality of biasing members 210 which extend from the cover, as shown in FIGS. 4, 5, and 6. These biasing members 210 will interact with the apertures 266 of the channel support 250 as described below to provide an additional retaining force upon the medical article.

As an additional retention mechanism, adhesives or surface treatments such as those described above with reference to the channel 260 may also be used upon the cover 200. These adhesives or surface treatments can be applied on the region of the cover which is located directly above the channel 260 when the cover 200 is placed in the closed position, such as the adhesive layer 270 shown in FIG. 20. In this way, in some modes of the cover and channel design, the treated surface of the cover can contact the medical article when the cover is closed.

Retainer Hinge Mechanism

Figure 11:
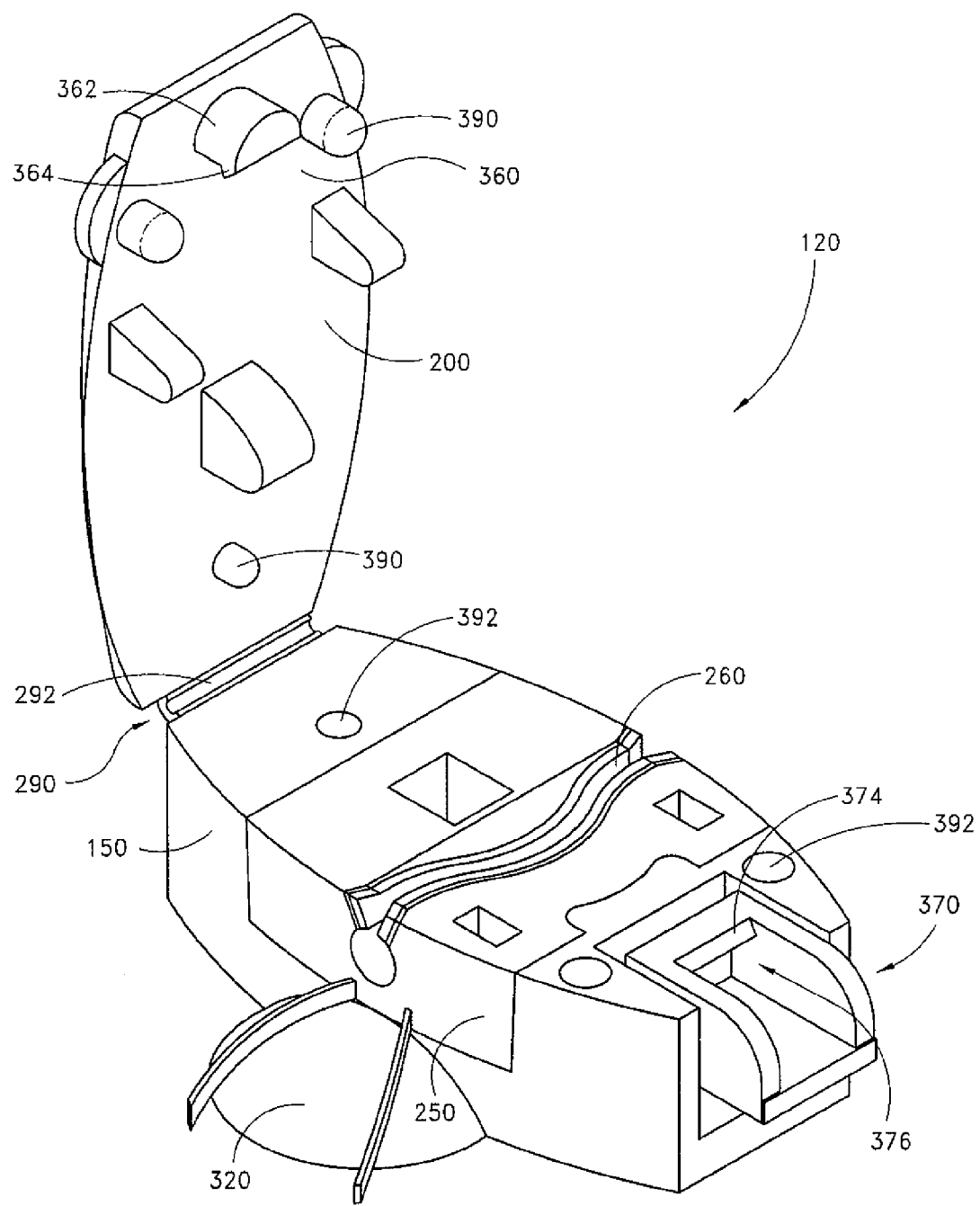
FIG. 11 shows a perspective view of the retainer of FIG. 4 with the cover in a partially open position.

As shown in FIG. 11, the cover 200 is flexibly coupled to the base 150 by way of the flexible coupling or hinge 290. The hinge desirably comprises a flexible band 292 that can take any number of forms to mechanically connect the cover 200 to the base 150 while permitting pivotal movement of the cover 200 relative to the base 150 so as to enable engagement or disengagement of these parts, as described below. In the illustrated embodiment, the band 292 is formed of flexible material, desirably of the same material from which the base 150 and cover 200 are constructed. Advantageously, the hinge 290 is integrally molded with the base 150 and the cover 200 to form a unitary member, as noted above. The hinge 290 is located at an outer edge of the base 150 and the cover 200; however, the hinge 290 need not be laterally located at an extreme end of the base or cover. The illustrated embodiment shows the hinge 290 positioned near the same plane as the upper edge of the base 150 for ease of manufacture.

As best understood from FIG. 7, the width of the hinge 290, as measured in the longitudinal direction, is desirably less than that of either the base 150 or the cover 200 to allow some leeway or play when engaging or disengaging the cover to the base. That is, this shape allows the hinge 290 to twist to some degree to compensate for manufacturing tolerances; however, the hinge can have at least as large of a longitudinal dimension as the base 150 and the cover 200.

The hinge 290 is desirably integrally formed along a common corresponding exterior surface of the cover 200 and base 150. In the illustrated embodiment, as best understood from FIG. 15, the hinge 290 generally has a U-shape when the cover 200 is closed, and extends from both the base 150 and the cover 200 in the lateral direction to the side of the retainer 120. A gap, corresponding to a transverse height of the hinge 290, exists between the base 150 and cover 200. This gap can be reduced or eliminated from the retainer 120 for some applications by using a different hinge design.

The hinge 290 enables the cover 200 to move between the open position and the closed position. The open position, as illustrated in FIG. 11, is characterized by exposing the channel 260 in the channel support 250 in the transverse direction and thereby spacing apart the base 150 and the cover 200. When in the open position, the channel 260 is capable of receiving a portion of the percutaneous drainage tube or other medical article. The closed position, as illustrated in FIG. 10, is characterized by the cover 200 lying in contact or near contact with the base 150 so as to position the cover 200 above the channel 260, sealing the channel in the transverse direction. When in the closed position, the retainer 120 surrounds the received portion of the tube or medical article (see FIG. 18).

The hinge 290 need not provide 180° of movement of the cover 200 relative to the base 150 to establish the closed position and a fully open position, as illustrated by FIGS. 4 and 10. For instance, the hinge 290 can permit a smaller degree of movement (e.g., 90°) between the base 150 and the cover 200 while still providing enough space to transversely insert the medical article into the retainer 120, as shown in FIG. 11.

Retainer Latch Mechanism

To firmly hold the percutaneous drainage tube within the channel 260, the base 150 and the cover 200 include interengaging structure to couple them together in the closed position. In the illustrated embodiment, as best seen in FIGS. 10 and 11, a latch mechanism 350 is used to secure the cover to the base. The latch mechanism comprises a keeper 360 and a latch 370. The keeper 360 is arranged on the cover 200 while the latch 370 is arranged on the base 150; however, these components can be conversely arranged with the keeper on the base and the latch on the cover. The latch mechanism 350 desirably is formed with the base 150 and cover 200 as a unitary piece.

As best seen in FIG. 11, the keeper 360 depends from the cover 200. The illustrated keeper is generally L-shaped, having a first bar 362 extending toward the base 150 from the lower side of the cover 200 when the cover is in the closed position. The keeper 360 also has a second bar 364 formed at a lower end of the first bar 362. Desirably, the lower end of the second bar 364 is relatively blunt and smooth to prevent it from puncturing the gloves or skin of a healthcare worker or catching on other materials. The keeper, however, need not be generally L-shaped, but rather can be generally C-shaped, generally J-shaped, or comprise a singular angled bar or the like.

Figure 12:
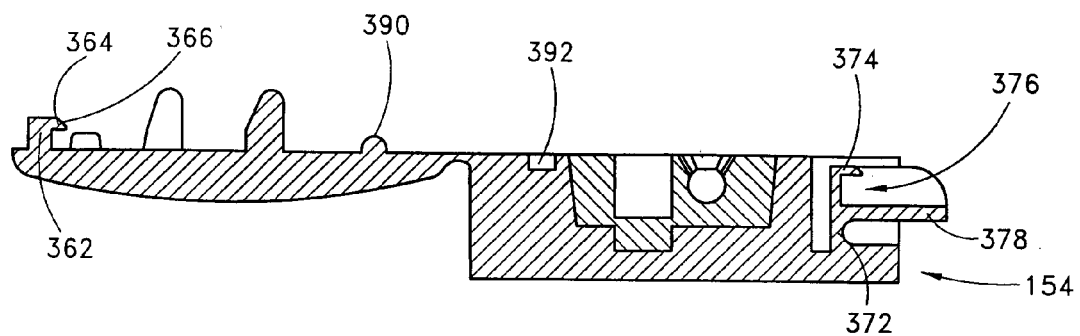
FIG. 12 shows a front cross-sectional view of the retainer of FIG. 4 with the cover in the open position, highlighting the components of a latch mechanism.

The second bar 364 includes a chamfer 366 along at least a portion of the inner edge, as shown in FIG. 12. The chamfer 366 edge slopes away from the center of the cover 200 to assist in releasably engaging the base 150 and cover 200, as explained below.

FIGS. 11 and 12 also shows the interengaging structure further comprising a latch 370 extending from the second end 154 of the base 150. The latch 370 has an actuating bar 372, a tang 374, a recess 376, and an operator lever 378.

Referring to FIG. 12, the actuating bar 372 extends from the base 150 and couples the base to the other elements of the latch 370. The actuating bar 372 is configured so that at least a portion of the actuating bar, desirably the upper portion, can bend or give in the lateral direction when a suitable lateral force is applied. This configuration allows the tang 374 to displace centrally when the keeper 360 contacts the tang 374 so that the keeper 360 can advance over the tang 374 and into the recess 376, as detailed below and shown in FIG. 14.

The tang 374 extends from the actuating bar 372 in the lateral direction. The tang 374 defines a ridge having an underside which is suitably sized to accept and retain the keeper 360, as described below. The free lateral edge of the tang 374 includes a chamfer. The chamfered edge slopes away from the center of the base 150 to facilitate insertion of the keeper 360 into the latch 370 and thereby assist in releasably engaging the base 150 and the cover 200.

The recess 376 is arranged to receive at least a portion of the second bar 364 of the keeper 360 when the cover 200 is moved to the closed position. The recess 376 provides an open area defined by the actuating bar 372, the tang 374 and the operator lever 378. The recess 376, however, can be arranged on the keeper 360 and the second bar 364 arranged on the latch 370 to accomplish the same effect.

Figure 13:
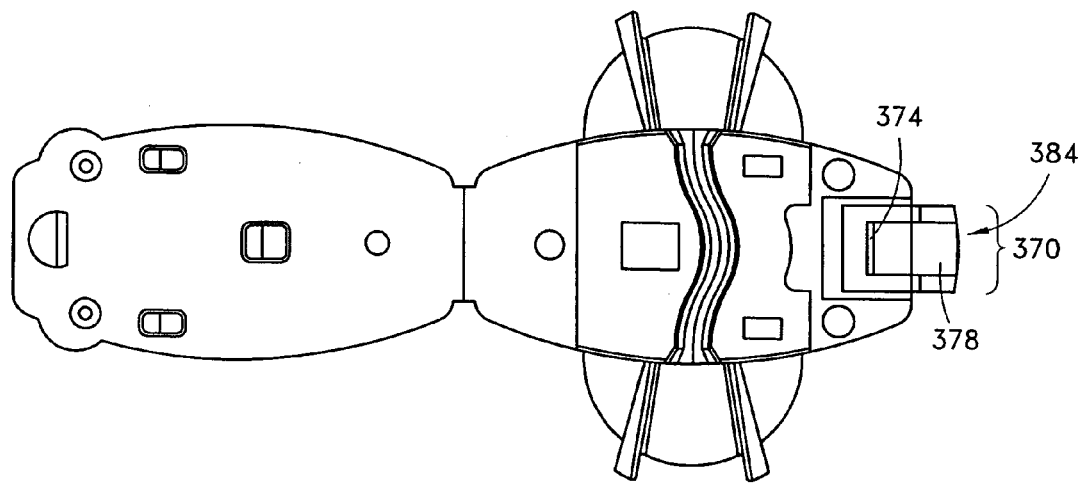
FIG. 13 shows a top view of the retainer of FIG. 4 with the cover in the open position, highlighting the components of the latch mechanism.

The operator lever 378 extends from the actuating bar 372 in the lateral direction and desirably protrudes beyond the second end 154 of the base 150 to allow a component of a suitable force to deflect the actuating bar 372 in the lateral direction toward the center of the base 150. The operator lever 378 desirably has a hollow region adjacent the recess 376 to accept at least a portion of the keeper 360 when the cover 200 is moved to the closed position. The operator lever 378 shown in FIG. 13 is generally U-shaped (as viewed from above); however, a variety of other configurations can be used. The free lateral edge 384 of the operator lever 378 can include a curvature to generally match the curvature of a fingertip to assist a healthcare worker in pushing on the operator lever 378 and for other ergonomic purposes. The free lateral edge 384 can also include ridges or knurls (not shown) to assist in maintaining secure contact between the healthcare worker's finger tip and the operator lever 378.

Figure 14:
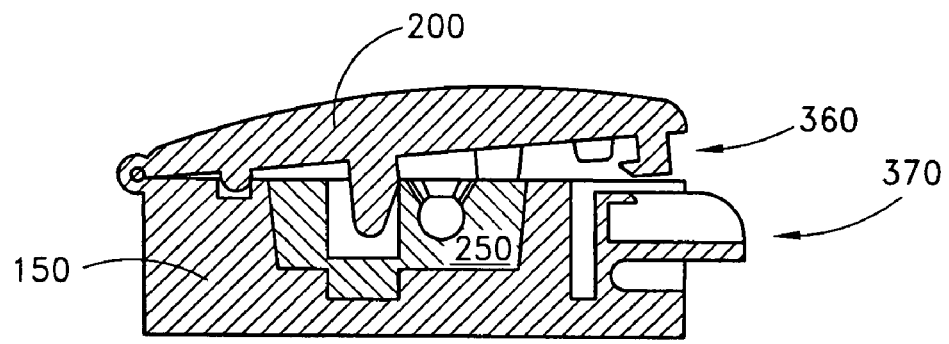
FIG. 14 shows a front cross-sectional view of the retainer of FIG. 4 as the cover approaches the closed position, just as the components of the latch mechanism make contact.
Figure 15:
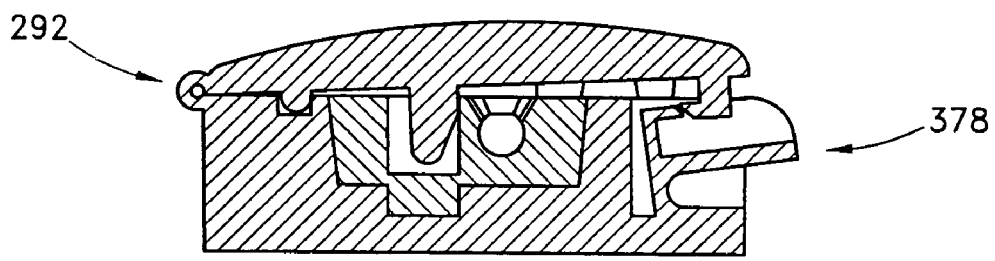
FIG. 15 shows a front cross-sectional view of the retainer of FIG. 4 as the components of the latch mechanism deflect against each other.
Figure 16:
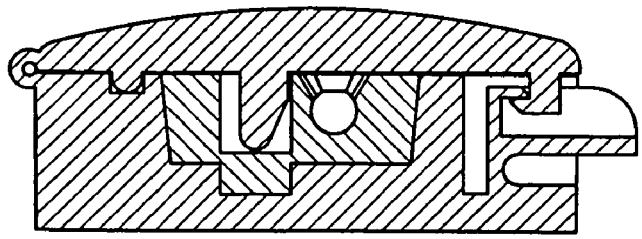
FIG. 16 shows a front cross-sectional view of the retainer of FIG. 4 as the latch mechanism locks into the closed position.

The operation of the latching mechanism 350 is shown in the progression of FIGS. 14, 15, and 16. The cover 200 swings from the open position toward the closed position. The relatively thin strip of material 292 forming the hinge 290 bends when finger pressure is exerted on the cover 200 to close it. As the cover nears its closed position, at least a portion of the keeper 360 advances into the hollow of the operator lever 378, and the chamfer edge 366 of the second bar 364 of the keeper 360 contacts the chamfer edge of the tang 374 of the latch 370. Continued pressure on the cover 200 is transferred through the chamfers to the actuating bar 372, and forces the tang 374 and the actuating bar 372 to deflect inward toward the channel 260. These forces also cause the first bar 362 of the keeper 360, and thus the second bar 364, to deflect outward, i.e., away from the channel 260. The recess 376 then receives at least a portion of the second bar 364 of the keeper 360 as the keeper is pushed further into the hollow. In this manner, at least portion of the latch 370 (specifically, the tang 374) acts as a gatekeeper or moveable entranceway which selectively allows for passage of at least a portion of the keeper 360 (specifically, the second bar 364) into the recess 376.

As shown in FIG. 16, when the second bar 364 extends below the tang 374 and the cover 200 sits atop the base 150, the actuating bar 372 and the first bar 362 snap back under the spring force provided by their deflection to position the second bar 364 beneath the tang 374 within the recess 376 of the latch 370. In this position, the keeper 360 and the latch 370 are interlocked together as the tang 374 obstructs passage of the second bar 364 through the entranceway. The interaction between the keeper 360 and the latch 370, together with the obstructed passage, holds the base 150 and cover 200 in this closed position.

To open the latch mechanism 350, the healthcare worker presses on the operator lever 378 in the lateral direction so that the operator lever 378 exerts an inward force that deflects the actuating bar 372 in the lateral direction toward the channel 260. Inward deflection of the actuating bar 372 inwardly deflects the tang 374, which, in turn, opens the entranceway so that the second bar 364 can be released from the recess 376. The healthcare worker can then open the cover 200 and expose the channel 260.

With reference to FIGS. 10 and 11, a transverse force can be used to open the cover 200 and assist in moving the keeper 360 away from the latch 370. The transverse force can be applied through a variety of mechanisms. One such mechanism involves the hinge 290, where the inherent spring force stored in the bent band of material 292 forming the hinge 290 provides the suitable transverse force.

Another such mechanism involves one or more interengaging elements arranged between interfacing portions of the base 150 and the cover 200. The embodiment illustrated in FIG. 11 shows three sets of interengaging elements, one set arranged near the hinge 290 and two sets arranged near the latch mechanism 350. Each set of interengaging elements include a pin 390 that depends from the cover 200 and a receiver 392 that recedes into the base 150. The pin 390 is configured to fit within the receiver 392 so that when the cover 200 is closed, the pin 390 extends into the receiver 392 to interlock the base 150 and cover 200 together. The transverse length of the pin 390 is desirably sized slightly larger than the transverse depth of the receiver 392 (e.g., about 0.05-0.5 mm). By this arrangement, when the cover 200 is in the closed position, the first end 204 of the cover 200 is offset from (i.e., not in contact with) the first end 152 of the base 150. Thus, the internal spring force stored in the interengaging elements 390, 392 can also provide a suitable transverse force to assist in opening the cover 200. The interengaging elements also serve to interlock the base 150 and the cover 200 in the longitudinal and lateral directions.

The releasable engagement between the cover 200 and the base 150 allows the same retainer 120 to be used for an extended period of time, while permitting repeated attachment and reattachment of the medical article to the anchoring system 100. In addition, the hinged connection 290 connecting the cover 200 to the base 150 ensures that the cover will not be lost or misplaced when the medical article is detached from the anchoring system 100. The healthcare worker wastes no time in searching for a cover in orienting the cover prior to latching.

Manufacturing

As stated above, the separate components of the described embodiment of the present anchoring system have different material requirements. The anchor pad 110, as described above, is best constructed from flexible laminates of foam or by layering textile surfaces over a foam core. With regard to the retainer 120, the base 150, cover 200, hinge 290, inner portions of the guide extensions 300 and latching mechanism 350 are best constructed from substantially rigid materials. Conversely, the channel support 250 and outer support surfaces 320 of the guide extensions 300 of the retainer 120 are best constructed using more pliant, elastic materials. As a result, it is desirable that different components of the retainer be made of different materials, as shown in FIG. 20.

As is apparent from the above description of the hinge 290 and latching mechanism 350, several features of the retainer 120 are desirably flexible. Suitable rigid but flexible materials include, for example, but without limitation, plastics, polymers or composites such as polypropylene, polyethylene, polyvinylchloride, acrylonitrile butadiene styrene, nylon, olefin, polyester, as well as moldable silicon, thermoplastic urethane, thermoplastic elastomers, thermoset plastics and the like. These materials provide for the needed flexibility in constructing the hinge and latch means, while also retaining sufficient rigidity to be appropriate for construction of the base and cover. The illustrated retainer 120 preferably is formed by injection molding using polyethylene or polypropylene (e.g., 30% calcium filled polypropylene) material. However, other materials can be utilized, and the retainer can comprise a non-unitary base and cover. Thus, for instance, where less flexibility is required in the hinge and latch mechanism designs, polycarbonate and acrylic materials are also suitable.

The material from which the channel support 250 and guide extension outer surfaces 320 are constructed should be more pliable and compressible than the material described above for use in constructing the base 150, cover 200, hinge 290 and latching mechanism 350. This is because the channel 260 and support surface 320 of the guide extensions 300 is desirably deformable to the extent that they can form a substantially continuous contact with the surface of the medical article being retained in order to provide the maximum possible support at all points along the supported length of the medical article. The outer surfaces 320 of the guide extensions 300, however, need not be made of the same pliable and compressible material as the channel support 250, and can rather be formed of the same material from which the base 150 is constructed. In this mode, the inner portion and outer surface of the guide extensions are unitarily formed.

Materials which are suitably elastic and compressively deformable include Kraton® polymer compounds, such as Dynaflex® G2706 available from GLS Corporation, as well as other thermoplastic elastomers or silicone or urethane epoxies. The Dynaflex compound used in the preferred embodiment illustrated has a Shore A hardness of about 28 durometer. Suitable materials preferably have hardness of no more than 50 durometer, and more preferably no more than 40 durometer. Dynaflex can be formed into the channel support 250 and guide extension 300 shapes through traditional injection molding processes.

In addition to separate construction of the channel support 250 via injection molding, it is also possible to integrally form the entire retainer, even though different materials are used for the rigid but flexible parts (base, cover, hinge, latch) and the pliant and elastic parts (channel support, guide extension). This method involves a two-stage injection over-molding process. The base 150, cover 200, hinge 290, inner guide extensions and latching mechanism 350 are formed in the first phase of the over-molding process using one of the harder materials described above, such as 30% calcium filled polypropylene.

The channel support 250 and guide extension outer surfaces 320 are formed in the second stage of the over-molding process using a Kraton compound such as Dynaflex, described above. This second phase of molding will mold the channel support and guide extension surfaces in position upon the base 150, affixing them in their appropriate positions.

By using this method, the entire retainer 120 can be formed unitarily and without involving the extra steps of mechanically joining separately manufactured parts. However, if the channel support 250 and guide extensions 300 are to be manufactured separately from the rest of the retainer 120, they may be attached to the base 150 by various means known in the art, including but not limited to adhesive bonding and ultrasonic welding. It will be recognized that other materials or manufacturing processes as known in the art may also be used.

Operation

Figure 3:
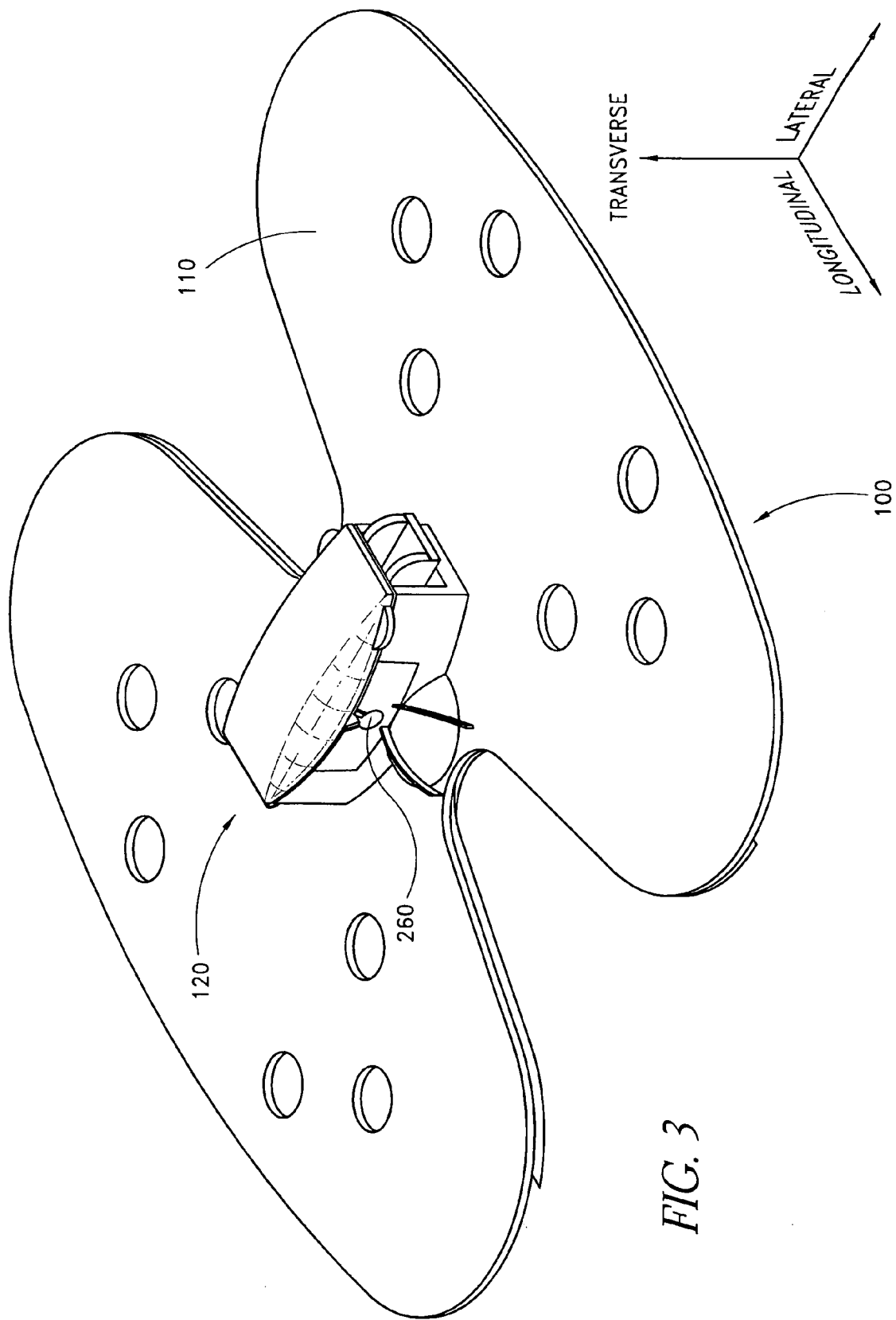
FIG. 3 shows a perspective view of the anchoring system of FIG. 1 with the cover in a closed position.
Figure 17:
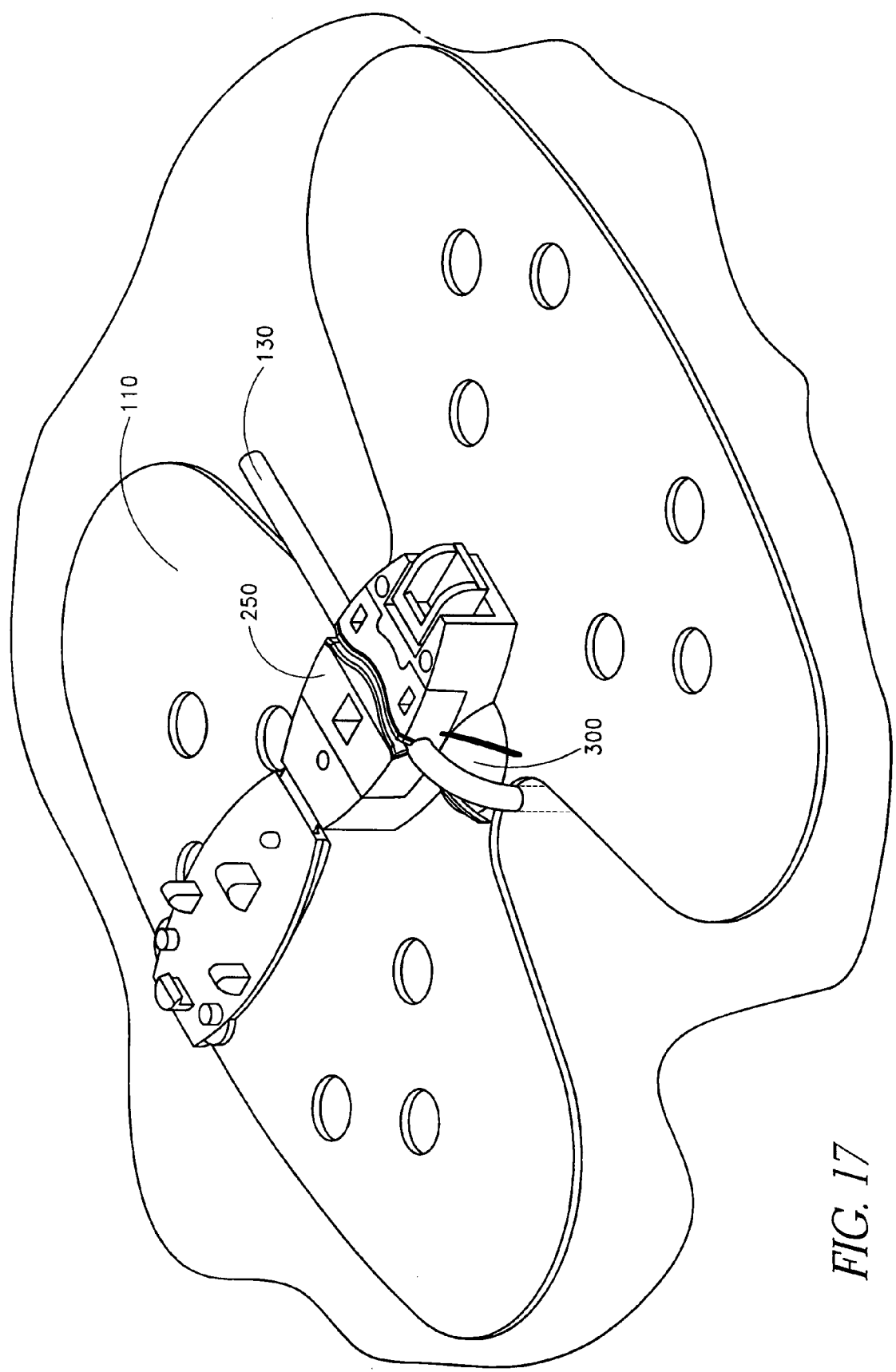
FIG. 17 shows a perspective view of an exemplary percutaneous drainage tube after insertion into the retainer of FIG. 1.

In operation, the described embodiment is used to secure a medical article to a patient as described below. With reference to FIG. 1, the healthcare worker will first insert the distal end of the percutaneous drainage tube or other medical article to be secured into the patient. The device of the present embodiment is then attached to the percutaneous drainage tube. This is done by moving the cover 200 of the retainer 120 into the open position (if necessary) as shown in FIG. 3, which will expose the channel 260 within the retainer 120 in the transverse direction. A length of the elongated portion of the medical article 130 is then pressed into the channel 260 of the retainer 120 from above, as shown in FIG. 17. Because the material from which the channel support 250 is formed is pliant and elastic, medical articles 130 with diameters slightly larger than that of the channel 260 itself may be secured within the channel in this way.

Once the medical article 130 is within the channel 260 of the retainer 120, the anchoring system 100 is attached to the skin of the patient. First, the skin of the patient near the insertion site is prepared according to normal antiseptic protocol, and then the healthcare worker removes the release liner 114 of the anchor pad 110 and presses the anchor pad onto the patient's skin such that the insertion site of the medical article lies generally within the space defined by the concave shape 122 on one side of the anchor pad 110.

Once the anchor pad 110 is positioned, the medical article 130 may be positioned such that the length of the medical article which extends from the channel 260 to the insertion site lies against the support surface 320 of the guide extension 300 between the channel 260 and the insertion site. This can be done by pulling on the medical article 130 until it lies snug against the support surface 320.

Once the medical article 130 is positioned as desired, the cover 200 is moved toward the closed position. The thin strip of material 292 forming the hinge coupling 290 allows the hinge to bend when finger pressure is exerted on the cover 200 to close it. The latch mechanism 350 will operate as described above between the cover 200 and the base 150 as the cover nears its closed position. As the cover 200 is pressed downward, the tang 374 will deflect and then snap into position with the keeper 360. This interaction between the tang 374 and the surfaces of the keeper 360 hold the cover 200 in the closed position.

As the cover 200 moves into the closed position, the biasing members 210 that are located upon the cover will descend into the apertures 266 located on the channel support 250 (see FIG. 11). The biasing members 210 have at least one side which is angled with respect to the channel support 250, producing a "shark-fin" profile to the biasing members 210.

When the biasing members 210 descend into their apertures 266, they will press against the surface of the apertures within the channel support 250, and generally produce a gentle squeezing upon the channel 260. Because the material of the channel support 250 is pliant and compressible, this squeezing will not be concentrated at a single point, but will be distributed along the side of the channel 260 adjacent to the aperture 266 where the biasing member 210 produces the pressure. In this way, compressive stress is produced along the length of the channel 260 which attempts to squeeze the channel down to a narrower diameter. This allows medical articles 130 with diameters less than the diameter of the channel 260 to be securely retained.

These compressive stresses which are imposed upon the channel support 250 (or other compressible member) tend to distort the shape of the channel support somewhat. This is because the channel support is formed from an elastic material. However, once the cover 200 is in the closed position, the channel support 250 is effectively prevented from deforming substantially in any lateral or transverse direction. The cover 200 and base 150 restrain the channel support 250 in the transverse direction, and the sides of the cavity 156 restraint the channel support 250 laterally. The channel support may deform inwardly somewhat, compressing the channel 260 and decreasing its size, but only to the extent that the medical article is able to be compressed inwardly.

The channel support 250 is unrestrained on its first and second longitudinal ends 254, 256, and is therefore capable of deforming in these directions. The base and the cover, however restrain the channel support 250 over a greater surface area than the combined surface area of the first and second longitudinal ends 254, 256. Accordingly, only a limited amount of distortion (if any) of the channel support 250 occurs in the longitudinal direction.

As the cover 200 reaches the closed position and is held in position by the latching mechanism 350, any adhesive or other surface treatments applied to the cover 200 (as described above) will come into contact with the medical article 130 and exert additional force to further inhibit undesirable motion of the medical article if this variation is used.

Figure 18:
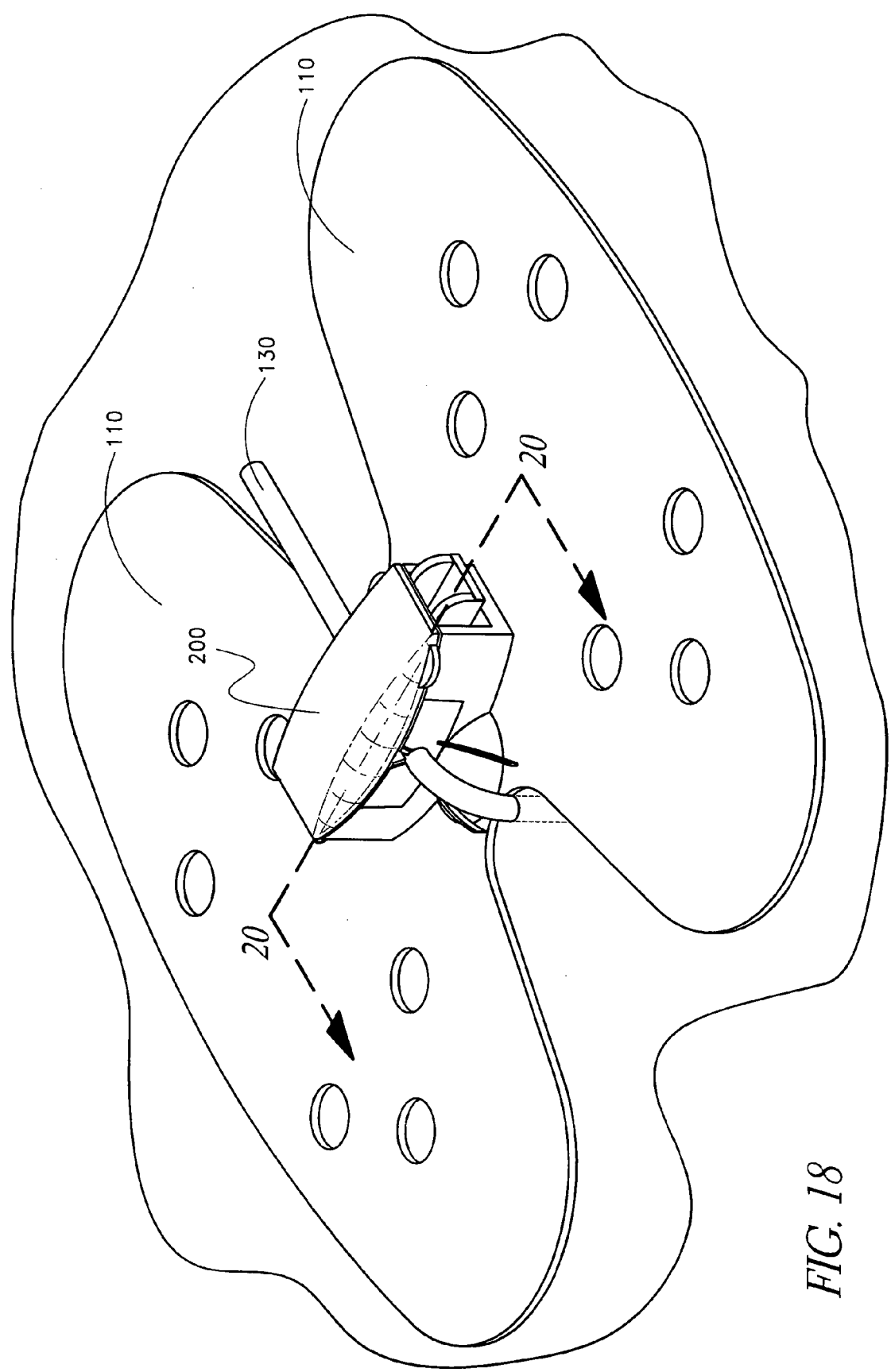
FIG. 18 shows a perspective view of an exemplary percutaneous drainage tube secured into position within the closed retainer of the device of FIG. 1.

In the position shown in FIG. 18, the medical article 130 is now securely anchored to the patient, and undesirable motion in the longitudinal, transverse, and lateral directions is now inhibited by the retainer 120. The length of the medical article 130 that is held within the channel 260 is surrounded by the channel and the cover 200. The channel 260 will press upon the medical article 130 along the retained length from below and the sides, and the cover 200 will seal the channel 260 from above. In this way, inward pressure is exerted upon the medical article 130 along its retained length, as well as from more than 180 degrees around its circumference by the elastic material of the channel 260.

Because this pressure is exerted along the surface of the medical article 130 from multiple directions, the pressure at no point along the length of the retained portion of the medical article will be abruptly greater than any other point, and the medical article will not buckle or crimp, which might occlude the lumen of the medical article.

In this way, the serpentine channel 260 inhibits lateral motion of the medical article 130, and the interaction of the channel 260 and the cover 200 inhibits transverse motion of the medical article 130 once secured.

Axial motion of the medical article 130 is inhibited by the friction between the surface of the medical article and the sides of the channel 260. Even when used with medical articles which have diameters that are not larger than the diameter of the channel, the squeezing produced by the biasing members 210 will produce contact between the channel 260 and the medical article 130, creating the desired friction. Additionally, the curved path of the channel 260 will produce increased frictional forces on the medical article, as discussed below.

This frictional force is increased during the operation of the device in several manners. First, the frictional force is increased due to an increase in surface contact between the compressible member and the medical article due to the curvilinear shape of the channel, and to the lateral forces produced by the squeezing of the channel 260 upon the medical article 130 due to the pressure of the biasing members 210 on the apertures 266. In addition or in the alternative, the increase lateral forces can be produced by an interference between the compressible member and the medical article where the medical article has a larger diameter than the channel. Surface treatments or adhesives may also be placed upon the inner walls of the channel 260 and on the cover 200 to further increase the friction between the retainer 120 and the medical article 130, as discussed above. The curved path followed by the channel 260 further increases the friction.

One way in which the curved channel 260 increases the friction between the channel and the medical article 130 is by increasing the length of the channel. The shortest possible channel through the channel support 250 would be a straight channel normal to the sides of the channel support. However, a curved path is longer than the straight path would be, and this curved path will contact the medical article 130 along a greater length of the medical article, thereby producing more total frictional resistance to longitudinal movement, even when the friction is the same at any single point.

Another way in which the curved channel 260 increases the friction between the channel and the medical article 130 is by increasing the normal force between the channel and the medical article at certain points along the curve of the channel. The medical article 130 will press more strongly against the inner surface of any curve in the channel 260 (i.e., the side which is closer to the center of curvature for that part of the channel) than it would against a straight channel. This increased normal force will lead to increased friction between the channel and the medical article even if the coefficient of friction between the two surfaces remains the same.

The serpentine path of the channel 260 also produces a more even distribution of the pressure which is created by the biasing members 210 upon the apertures 266, as discussed above. Each biasing member 210 will press against a portion of the channel support 250, creating compressive stresses within the channel support (or other compressible member). Because of the elastically deformable nature of the material of the channel support, these stresses will generally propagate from the location at which the biasing member 210 contacts the aperture 266 within the channel support 250.

The magnitude of the compressive stress will slowly decrease as distance increases from the biasing member 210. As a result, the levels of constant compressive stress will tend to form a series of concentric curves centered roughly on the biasing member 210 and aperture 266 into which the member is placed.

By using a serpentine path for the channel 260, the channel can be made to follow along a path where the compressive stresses imposed upon the channel support 250 by the biasing members 210 are roughly constant. By following such a path of substantially constant compressive stresses, the amount of compressive force which is transferred to the medical article 130 held within the channel 260 is made more constant. By avoiding large fluctuations in the magnitude of the laterally compressive force upon the medical article 130, the medical article is less susceptible to crimping and kinking.

It is also possible to use a retainer base 150 which is hinged or otherwise flexes so as to apply lateral compression to the channel support 250 (or other compressible member) when the cover 200 is closed and the latch engaged to hold the retainer 120 closed.

Figure 19:
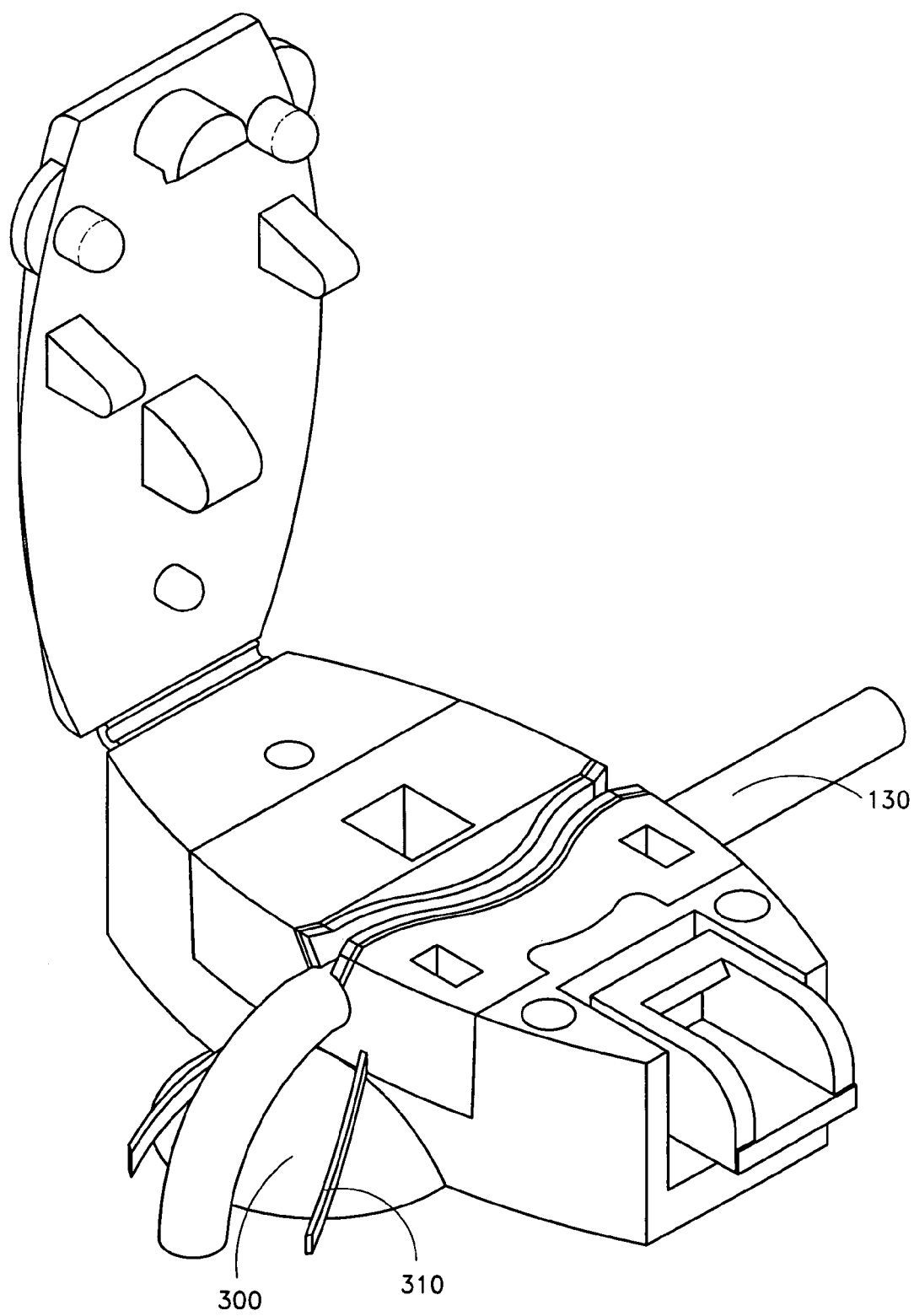
FIG. 19 shows a perspective view of the retainer of FIG. 4 with the cover in the open position and with an exemplary percutaneous drainage tube inserted into the retainer.

In addition to the support provided by the channel 260 to the medical article 130, the guide extension 300 also inhibits undesirable motion along the length of any portion of the medical article 130 which is secured against the guide extension 300 (see FIG. 18). Most importantly, the guide extension will inhibit crimping and buckling of the medical article 130 as it bends from running substantially parallel to the skin of a patient (as it passes through the channel 260) to running substantially angled to the skin of a patient (as it enters the skin at the insertion site). This transition is shown in FIG. 19.

Although support is only provided from one side by the support surface 320 of the guide extensions 300, buckling and crimping is still inhibited because the constant pressure of the guide extension along the length of the bending portion of the medical article 130 prevents any single region from folding inward to produce a buckle. In effect, the outward force of the support surface 320 against the medical article 130 puts the entire medical article into tension in the region of the bend, preventing any buckling, which can only occur when at least one side of the medical article is in compression. Furthermore, the guide ridges 310 of the guide extension 300 inhibit undesirable lateral displacement of the medical article 310 as it extends from the channel 260 to the insertion site.

This releasable engagement between the cover 200 and the base 150 allows the same retainer 120 to be used for an extended period of time, while permitting repeated attachment and reattachment of the medical article 130 to the anchoring system 100. In addition, the hinge 290 connecting the cover 200 to the base 150 ensures that the cover will not be lost or misplaced when the medical article 130 is detached from the anchoring system 100. The healthcare worker wastes no time in searching for a misplaced cover, nor in orienting a cover prior to latching.

An additional advantage of the described embodiment of the present invention is the ability to rapidly and effectively adjust the positioning of the medical article 130 within the anchoring system 100 without the need to reapply the entire anchoring device or otherwise replace the entire dressing. By moving the cover 200 to the open position, the increased axial motion inhibition on the medical article 130 due to the effect of the biasing members 210 in their apertures 266 and the friction between the cover 200 and the medical article 130 is relaxed. The healthcare worker can then simply pull the medical article axially away from the insertion site by grasping the portion of the medical article 130 which extends from the distal end 264 of the channel from the insertion site and pulling until the medical article 130 is snug against the guide extension surface 320 and the medical article is in correct relation to the insertion point.

This procedure is especially important when the anchoring system 100 is used with percutaneous drainage tubes used to drain abscesses or other swollen regions. As the swelling is reduced, the tube 130 will tend to migrate outwardly at the insertion site, introducing slack between the insertion site and the proximal side 262 of the channel 260. This slack undesirably allows the medical article 130 to lift off of the support surface 320 of the guide extension 300. Because the guide extension is no longer exerting force upon the medical article 130 which keeps it under tension, the tube may buckle or crimp, partially or completely occluding the lumen of the tube. By periodically opening the cover 200, pulling the medical article 130 to maintain tension between the retainer 120 and insertion site, and then closing the cover, the lumen can be maintained in a clear condition without the need to remove and reapply the anchoring system 100 or other medical dressings associated with the percutaneous drainage tube 130.

Another advantage of the described embodiment of the present invention relates to the sizes of medical articles 130 which are successfully secured by a particular sized channel 260. Because the material of the channel support 250 is elastic and pliant, it is possible to insert medical articles 130 which have outer diameters larger than the inner diameter of the channel 260 into the channel. Furthermore, because the channel is compressed laterally by the action of the biasing members 210 in their apertures 266, medical articles 130 with outer diameters less than the diameter of the channel 260 are still held securely when the cover 200 is moved into the closed position. As a result, a single channel 260 is capable of securing medical articles 130 which have a wide range of outer diameters, for example, the same anchoring system 100 could secure size 8 French to size 14 French tubes. This reduces the total number of different size channels which are needed to retain any expected size of medical article.

The various embodiments of anchoring systems described above in accordance with present invention thus provide a sterile, tight-gripping, needle- and tape-free way to anchor a medical article to a patient. The retainer thus eliminates use of tape, and if prior protocol required suturing, it also eliminates accidental needle sticks, suture-wound-site infections and scarring. In addition, the retainer can be configured to be used with any of a wide variety of catheters, fittings, tubes, wires, and other medical articles. Patient comfort is also enhanced and application time is decreased with the use of the present anchoring system.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the alternative channel shapes shown in FIGS. 8 and 9 can be adapted for use with any of the various bases, covers, hinges, anchor pads and latching mechanisms disclosed herein. In addition to the variations described herein, other known equivalents for each feature can be mixed and matched by one of ordinary skill in this art to construct anchoring systems in accordance with principles of the present invention.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method of anchoring a medical article onto a patient, which permits an axial position of the medical article to be repositioned relative to the patient, comprising:
    inserting a section of the medical article into a channel receptacle of a compressible member, the compressible member being supported by a base, the base comprising a first material and the compressible member comprising a second material, the second material being softer than the first material;
    producing a compressive stress within the compressible member so as to increase the normal force acting upon the inserted section of the medical article and thereby increase a frictional force between the inserted section of the medical article and the compressible member;
    applying a compression stress to the compressible member so as to produce said compressive stress acting upon the inserted section of the medical article, wherein the compression stress is applied by inserting a biasing member into an aperture of the compressible member in a manner creating interference between the biasing member and the compressible member which compresses the compressible member, the aperture not being part of the channel; and
    positioning a cover over at least a portion of the channel receptacle and securing the cover in a position overlying the portion of the channel receptacle.

2. A method as in claim 1 additionally comprising releasing the cover and moving the cover away from the receptacle, pulling the medical article through the channel receptacle so as to axially reposition at least a portion of the medical article, repositioning the cover over at least a portion of the channel receptacle and securing the cover in the overlying position.

3. A method as in claim 1 additionally comprising tracking a section of the medical article, which is adjacent to the inserted section of the medical article, over a curved support surface to inhibit kinking of the medical article.

4. A method as in claim 1, wherein the compressive stress is produced with a cover in an open position exposing at least a portion of the channel receptacle.

5. A method as in claim 1, wherein the compressible member is elastically deformable.

6. A method as in claim 1, wherein the second material is a thermoplastic elastomer.

7. A method as in claim 1, wherein the second material has a Shore A hardness of no greater than 50 durometer.

8. A method as in claim 1, wherein the second material has a Shore A hardness of no greater than 28 durometer.

9. A method of anchoring a medical article onto a patient, comprising:
    providing a retainer including a base having an overall length in a longitudinal direction that is substantially parallel to an axis of the portion of the medical article being retained and a compressible member, the compressible member forming a receptacle, the base comprising a first material and the compressible member comprising a second material, the second material being softer than the first material;
attaching the retainer to the patient's skin, whereby the retainer does not cover an insertion site of the medical article;
inserting a section of the medical article into the receptacle of the compressible member;
deforming a portion of the compressible member in a manner that produces compressive stresses within the compressible member that bear against the section of the medical article when received within the receptacle; and
applying a compression stress to the compressible member so as to produce said compressive stress bearing against the inserted section of the medical article, wherein the compression stress is applied by inserting a biasing member into an aperture of the compressible member in a manner creating interference between the biasing member and the compressible member which compresses the compressible member, the aperture not being part of the receptacle.

10. A method as in claim 9 additionally comprising positioning a cover over at least a portion of the receptacle and securing the cover in a position overlying the portion of the receptacle.

11. A method as in claim 10 additionally comprising releasing the cover and moving the cover away from the receptacle, pulling the medical article through the receptacle so as to axially reposition at least a portion of the medical article, repositioning the cover over at least a portion of the receptacle and securing the cover in the overlying position.

12. A method as in claim 10, wherein the cover does not cover the insertion site of the medical article when the cover is secured in the position overlying the portion of the receptacle.

13. A method as in claim 9 additionally comprising tracking a section of the medical article, which is adjacent to the inserted section of the medical article, over a curved support surface to inhibit kinking of the medical article.

14. A method of anchoring a medical article onto a patient, comprising:
providing an anchor pad having a first side including an adhesive layer to adhere the anchor pad to a patient's skin and having an opposing second side;
providing a retainer attached to the opposing second side, the retainer including, a base having an overall length in a longitudinal direction that is substantially parallel to an axis of a portion of the medical article being retained, a compressible member, and a cover pivotally attached to the base and having first and second sides, the first and second sides being spaced apart in the longitudinal direction with the compressible member disposed therebetween; and
positioning the portion of the medical article against the compressible member, wherein the medical article extends generally in the longitudinal direction beyond the first and second sides of the cover when the medical article is placed within the retainer and the cover is in the closed position.

15. A method as in claim 14 additionally comprising releasing the cover and moving the cover away from the compressible member, pulling the medical article through the compressible member so as to axially reposition at least a portion of the medical article, repositioning the cover over at least a portion of the compressible member and securing the cover in the overlying position.

16. A method as in claim 14 additionally comprising tracking a section of the medical article, which is adjacent to the inserted section of the medical article, over a curved support surface to inhibit kinking of the medical article.

17. A method as in claim 14 additionally comprising applying a compression stress to the compressible member so as to produce said compressive force.

18. A method as in claim 17, wherein the compression stress is applied by inserting a biasing member into an aperture of the compressible member in a manner creating interference between the biasing member and the compressible member which compresses the compressible member.

19. A method of anchoring a medical article onto a patient, comprising:
inserting a section of the medical article into a channel receptacle of a compressible member, the channel having at least two directional changes along its length;
producing a compressive stress within the compressible member so as to increase the normal force acting upon the inserted section of the medical article and thereby increase a frictional force between the inserted section of the medical article and the compressible member; and
inserting a biasing member into an aperture of the compressible member in a manner creating interference between the biasing member and the compressible member which compresses the compressible member against the inserted section of the medical article, the aperture not being part of the channel.

20. A method as in claim 19 additionally comprising positioning a cover over at least a portion of the channel receptacle and securing the cover in a position overlying the portion of the channel receptacle.

21. A method as in claim 20 additionally comprising releasing the cover and moving the cover away from the receptacle, pulling the medical article through the channel receptacle so as to axially reposition at least a portion of the medical article, repositioning the cover over at least a portion of the channel receptacle and securing the cover in the overlying position.

22. A method as in claim 19 additionally comprising tracking a section of the medical article, which is adjacent to the inserted section of the medical article, over a curved support surface to inhibit kinking of the medical article.

23. A method as in claim 19 additionally comprising applying a compression stress to the compressible member so as to produce said compressive force.

* * * * *